(12) United States Patent
Vaughan et al.

(10) Patent No.: US 6,451,557 B1
(45) Date of Patent: Sep. 17, 2002

(54) METHOD FOR PRODUCING, IN YEAST, A HYDROXYLATED TRIPLE HELICAL PROTEIN, AND YEAST HOST CELLS USEFUL IN SAID METHOD

(75) Inventors: Paul Richard Vaughan, Wheelers Hills (AU); Maria Galanis, Glen Waverley (AU); John Alan Maurice Ramshaw, Pascoe Vale (AU); Jerome Anthony Werkmeister, Camberwell (AU)

(73) Assignee: Commonwealth Scientific and Industrial Research Organisation, Act (AU)

( * ) Notice: Subject to any disclaimer, the term of this patent is extended or adjusted under 35 U.S.C. 154(b) by 0 days.

(21) Appl. No.: 09/297,269

(22) PCT Filed: Oct. 29, 1997

(86) PCT No.: PCT/AU97/00721

§ 371 (c)(1),
(2), (4) Date: Apr. 28, 1999

(87) PCT Pub. No.: WO98/18918

PCT Pub. Date: May 7, 1998

(30) Foreign Application Priority Data

Oct. 29, 1996 (AU) ............................................. PO-3310
Dec. 19, 1996 (AU) ............................................. PO-4306

(51) Int. Cl.[7] ............................. C12P 21/02; C12N 1/19
(52) U.S. Cl. .............. 435/69.1; 435/254.2; 435/254.21; 435/254.23
(58) Field of Search .......................... 435/69.1, 254.2, 435/254.21, 254.23

(56) References Cited

U.S. PATENT DOCUMENTS 5,593,859 A * 1/1997 Prockop et al. ............ 435/69.1
5,821,089 A * 10/1998 Gruskin et al.

FOREIGN PATENT DOCUMENTS

JP       08023979     1/1996
WO       WO 97/14431  4/1997

OTHER PUBLICATIONS

Romanos et al., Yeast 8: 423–488, Foreign gene expression in yeast: a review, 1992.*
Monaco et al., TIBTECH 12: 280–286, YACs, BACs, PACs and MACs: artificial chromosomes as research, 1994.*
<http://www.ncbi.nlm.nih.gov80/entrez/>, Accession No. NM_001844, accessed Jun. 5, 2000, 1989.*
Lamberg et al, *J. Biol. Chem.*, 271 (20):11988–11995 (1996).
Tomita et al, *Biochem. J.*, 312:847–853 (1995).
Veijola et al, *J. Biol. Chem.*, 269 (43):26746–26753 (1994).
Armstrong et al, *Biochimica et Biophysica Acta*, 1264:93–102 (1995).
Krol et al, *J. Invest. Dermatology*, 106(1):11–16 (1996).
Helaakoski et al, *Proc. Natl. Acad. Sci., USA*, 92:4427–4431 (1995).
Vuori et al, *Proc. Natl. Acad. Sci., USA*, 89:7467–7470 (1992).
Bulleid et al, *Biochem. J.*, 317:195–202 (1996).

* cited by examiner

*Primary Examiner*—Robert A. Schwartzman
(74) *Attorney, Agent, or Firm*—Sughrue Mion, PLLC

(57) ABSTRACT

A method for producing a hydroxylated triple helical protein is disclosed, as well as a yeast host cell used in the method. The method comprises culturing a yeast host cell comprising: (1) a first DNA molecule comprising a DNA sequence encoding P4Hα subunit operably linked to a promoter functional in the yeast host cell, (2) a second DNA molecule comprising a DNA sequence encoding P4Hα subunit operably linked to a promoter functional in the yeast host cell, and (3) a third DNA molecule comprising a DNA sequence encoding a polypeptide or peptide operably linked to a promoter functional in the yeast host cell, wherein the polypeptide or peptide is one which, when hydroxylated, forms the hydroxylated triple helical protein; and wherein during culturing, each of the first DNA molecule, the second DNA molecule and the third DNA molecule are replicated, stably retained and segregated.

60 Claims, 8 Drawing Sheets

Figure 2

```
   1 CCAGGCCCAC TTGGGATTGC TGGGATCACT GGAGCACGGG GTCTTGCAGG ACCACCAGGC
  61 ATGCCAGGTC CTAGGGGAAG CCCTGGCCCT CAGGGTGTCA AGGGTGAAAG TGGGAAACCA
 121 GGAGCTAACG GTCTCAGTGG AGAACGTGGT CCCCCTGGAC CCCAGGGTCT TCCTGGTCTG
 181 GCTGGTACAG CTGGTGAACC TGGAAGAGAT GGAAACCCTG GATCAGATGG TCTTCCAGGT
 241 CGAGATGGAT CTCCTGGTGG CAAGGGTGAT CGTGGTGAAA ATGGCTCTCC TGGTGCCCCT
 301 GGCGCTCCTG GTCATCCAGG CCCACCTGGT CCTGTCGGTC CAGCTGGAAA GAGTGGTGAC
 361 AGAGGAGAAA GTGGCCCTGC TGGCCCTGCT GGTGCTCCCG GTCCTGCTGG TTCCCGAGGT
 421 GCTCCTGGTC CTCAAGGCCC ACGTGGTGAC AAAGGTGAAA CAGGTGAACG TGGAGCTGCT
 481 GGCATCAAAG GACATCGAGG ATTCCCTGGT AATCCAGGTG CCCCAGGTTC TCCAGGCCCT
 541 GCTGGTCAGC AGGGTGCAAT CGGCAGTCCA GGACCTGCAG GCCCCAGAGG ACCTGTTGGA
 601 CCCAGTGGAC CTCCTGGCAA AGATGGAACC AGTGGACATC CAGGTCCCAT GGACCACCA
 661 GGGCCTCGAG GTAACAGAGG TGAAAGAGGA TCTGAGGGCT CCCCAGGCCA CCCAGGGCAA
 721 CCAGGCCCTC CTGGACCTCC TGGTGCCCCT GGTCCTTGCT GCGGTGGTGT TGGAGCCGCT
 781 GCCATTGCTG GGATTGGAGG TGAAAAAGCT GGCGGTTTTG CCCCGTATTA TGGACCTGAA
 841 CCAATGGATT TCAAAATCAA CACCGATGAG ATTATCACTT CACTCAAGTC TGTTAATGGA
 901 CAAATAGAAA GCCTCATTAG TCCTGATGGT CTCGTAAAA ACCCCGCTAG AAACTGCAGA
 961 GACCTGAAAT TCTGCCATCC TGAACTCAAG ACTGGAGAAT ACTGGGTCGA CCCTAACCAA
1021 GGATGCAAAT TGGATGCTAT CAAGGTATTC TGTAATATGG AAACTGGGGA AACATGCATA
1081 AGTGCCAATC CTTTGAATGT TCCACGGAAA CACTGGTGGA CAGATTCTAG TGCTGAGAAG
1141 AAACACGTTT GGTTTGGAGA GTCCATCGAT GGTGGTTTTC AGTTTAGCTA CGGCAATCCT
1201 GAACTTCCTG AAGATGTCCT TGATGTGCAG CTGGCATTCC CTCGACTTCT CTCCAGCCGA
1261 GCTTCCCAGA ACATCACATA TCACTGCAAA AATAGCATTG CATACATGGA TCAGGCCAGT
1321 GGAAATGTAA AGAAGGCCCT GAAGCTGATG GGGTCAAATG AAGGTGAATT CAAGGCTGAA
1381 GGAAATAGCA AATTCACCTA CACAGTTCTG GAGGATGGTT GCACGAAACA CACTGGGGAA
1441 TGGAGCAAAA CAGTCTTTGA ATATCGAACA CGCAAGGCTG TGAGACTACC TATTGTAGAT
1501 ATTGCACCCT ATGACATTGG TGGTCCTGAT CAAGAATTTG GTGTGGACGT TGGCCCTGTT
1561 TGCTTTTTAT AA
```

Figure 8

```
     EcoRI
        NcoI
  1 G AATTCCATG GGTGCTCCAG GTGCTCCAGG TGGTAAGGGT GACGCTGGTG CTCCAGGTGA
      N S M    G A P      G A P  G    G K G      D A G      A P G  E

61 AAGAGGTCCA CCAGGTTTGG CTGGTGCTCC AGGTTTGAGA GGTGGTGCTG GTCCACCAGG
     R G P     P G L      A G A P    G L R      G G A      G P P G

Bsp120I
121 TCCAGAAGGT GGTAAGGGTG CTGCTGGTCC ACCAGGTCCA CCAGGTGGGC CCGGTGGTAA
     P E G    G K G      A A G P    P G P      P G G      P G G K

181 GGGTGACGCT GGTGCTCCAG GTGAAAGAGG TCCACCAGGT TTGGCTGGTG CTCCAGGTTT
     G D A    G A P      G E R G    P P G      L A G      A P G L

241 GAGAGGTGGT GCTGGTCCAC CAGGTCCAGA AGGTGGTAAG GGTGCTGCTG GTCCACCAGG
     R G G    A G P      P G P E    G G K      G A A      G P P G

BssHII
301 TCCACCAGGT GCGCGCGGTG GTAAGGGTGA CGCTGGTGCT CCAGGTGAAA GAGGTCCACC
     P P G    A R G      G K G D    A G A      P G E      R G P P

361 AGGTTTGGCT GGTGCTCCAG GTTTGAGAGG TGGTGCTGGT CCACCAGGTC AGAAGGTGG
      G L A   G A P      G L R G   G A G      P P G      P E G G

421 TAAGGGTGCT GCTGGTCCAC CAGGTCCACC AGGTCCACCA GGTCCACCAG GTTGTTGTGG
      K G A    A G P    P G P      P G P      P G P      P G C C G

.XhoI    SacII     NheI
481 TCTCGAGGGT CCGCGGGGCT AGC
     L E G    P R G      -
```

METHOD FOR PRODUCING, IN YEAST, A HYDROXYLATED TRIPLE HELICAL PROTEIN, AND YEAST HOST CELLS USEFUL IN SAID METHOD

CROSS-REFERENCE TO RELATED APPLICATION

This Application is a National stage filing under 35 U.S.C. §371 of PCT/AU97/00721, filed Oct. 29, 1997.

FIELD OF THE INVENTION

This invention relates to the production of hydroxylated triple helical proteins such as natural and synthetic collagens, natural and synthetic collagen fragments, and natural and synthetic collagen-like proteins, by recombinant DNA technology. In particular, the invention relates to a method for producing hydroxylated triple helical proteins in yeast host cells by introducing to a suitable yeast host cell, DNA sequences encoding the triple helical protein as well as prolyl 4-hydroxylase (P4H), in a manner wherein the introduced DNA sequences are stably retained and segregated by the yeast host cells.

BACKGROUND OF THE INVENTION

The collagen family of proteins represents the most abundant protein in mammals, forming the major fibrous component of, for example, skin, bone, tendon, cartilage and blood vessels. Each collagen protein consists of three polypeptide chains (alpha chains) characterised by a (Gly-X-Y)$_n$ repeating sequence, which are folded into a triple helical protein conformation. Type I collagen (typically found in skin, tendon, bone and cornea) consists of two types of polypeptide chain termed α1(I) and α2(I) [i.e. α1(I)$_2$α2(I)], while other collagen types such as Type II [α1(ll)$_3$] and Type III [α1(III)$_3$] have three identical polypeptide chains. These collagen proteins spontaneously aggregate to form fibrils which are incorporated into the extracellular matrix where, in mature tissue, they have a structural role and, in developing tissue, they have a directive role. The collagen fibrils, after cross-linking, are highly insoluble and have great tensile strength.

The ability of collagen to form insoluble fibrils makes them attractive for numerous medical applications including bioimplant production, soft tissue augmentation and wound/burn dressings. To date, most collagens approved for these applications have been sourced from animal sources, primarily bovine. While such animal-sourced collagens have been successful, there is some concern that their use risks serious immunogenicity problems and transmission of infective diseases and spongiform encephalopathies (e.g. bovine spongiform encephalopathy (BSE)). Accordingly, there is significant interest in the development of methods of production of collagens or collagen fragments by recombinant DNA technology. Further, the use of recombinant DNA technology is desirable in that it allows for the potential production of synthetic collagens and collagen fragments which may include, for example, exogenous biologically active domains (i.e. to provide additional protein function) and other useful characteristics (e.g. improved biocompatability and stability).

The in vivo biosynthesis of collagen proteins is a complex process involving many post translational events. A key event is the hydroxylation by the enzyme prolyl 4-hydroxylase (P4H) of prolyl residues in the Y-position of the repeating (Gly-X-Y)$_n$ sequences to 4-hydroxyproline. This hydroxylation has been found to be beneficial for nucleation of folding of triple helical proteins. For collagens, it is essential for stability at body temperature. Accordingly, the development of a commercially viable method for the production of recombinant collagen requires co-expression of P4H with the alpha chains. For mammalian host cells, co-expression of P4H will occur autonomously since these cells should naturally express P4H. However, for yeast host cells, which for reasons of cost, ease and efficiency are more attractive for expression of recombinant eukaryotic proteins, transformation with DNA sequences encoding P4H will also be required. Since P4H consists of α and β subunits of about 60 kDa and 60 kDa, yeast host cells for expression of recombinant collagen will require co-transformation with at least three exogenous DNA sequences (i.e., encoding an alpha chain, P4H α subunit and P4H α subunit) and stability problems would therefore be expected if cloned on three separate vectors or, alternatively, all on episomal type vector. Indeed, even under continuous selection pressure, many episomal type vectors suffer stability problems if they are large or are present at relatively low copy number. An object of the present invention is therefore to provide a method for expressing recombinant collagen and other triple helical proteins from yeast host cells wherein the introduced DNA sequences are stably retained and segregated independent of continuous selection pressure.

SUMMARY OF THE INVENTION

Thus, in a first aspect, the present invention provides a method of producing a hydroxylated triple helical protein in yeast comprising the steps of:

introducing to a suitable yeast host cell a first nucleotide sequence encoding P4H α subunit, a second nucleotide sequence encoding P4H β subunit and one or more product-encoding nucleotide sequences which encode(s) a polypeptide(s) or peptide(s) which, when hydroxylated, form the said hydroxylated triple helical protein, each of said first, second and product-encoding nucleotide sequences being operably linked to promoter sequences, and culturing said yeast host cell under conditions suitable to achieve expression of said first, second and product-encoding nucleotide sequences to thereby produce said hydroxylated triple helical protein; wherein said method is characterised in that the step of introducing the first, second and product-encoding nucleotide sequences results in the said first, second and product-encoding nucleotide sequences, together with their respective operably linked promoter sequences, being borne on one or more replicable DNA molecules that are stably retained and segregated by said yeast host cell during said step of culturing.

In a second aspect, the present invention provides a yeast host cell capable of producing a hydroxylated triple helical protein, said yeast host cell including a first nucleotide sequence encoding P4H α subunit, a second nucleotide sequence encoding P4H β subunit and one or more product-encoding nucleotide sequences which encode(s) a polypeptide(s) or peptide(s) which, when hydroxylated, form the said hydroxylated triple helical protein, each of said first, second and product-encoding nucleotide sequences being operably linked to promoter sequences, and wherein said first, second and product-encoding nucleotide sequences, together with their respective operably linked promoter sequences, are borne on one or more replicable DNA molecules that are stably retained and segregated by said yeast host cell.

In a third aspect, the present invention provides a triple helical protein produced in accordance with the method of the first aspect.

In a fourth aspect, the present invention provides a biomaterial or therapeutic product comprising a triple helical protein produced in accordance with the method of the first aspect.

DETAILED DISCLOSURE OF THE INVENTION

The method according to the invention requires that the first and second nucleotide sequences encoding the P4H α and β subunits and the product-encoding nucleotide sequences be introduced to a suitable yeast host cell in a manner such that they are borne on one or more DNA molecules that are stably retained and segregated by the yeast host cell during culturing. In this way, all daughter cells will include the first, second and product-encoding nucleotide sequences and thus stable and efficient expression of a hydroxylated triple helical protein product can be ensured throughout the culturing step and without the use of continuous selection pressure.

The method according to the invention can be achieved by; (i) integrating (e.g. by homologous recombination) one or more of the exogenous nucleotide sequences (i.e. one or more of the first, second and product-encoding nucleotide sequences) into one or more chromosome(s) of the yeast host cell, or (ii) including one or more of the exogenous nucleotide sequences within one or more vector(s) including a centromere (CEN) sequence(s). Alternatively, a combination of these techniques may be used or one or both of these techniques may be used in combination with the use of one or two high copy number plasmid(s) which include the remainder of the exogenous nucleotide sequences. For example, the first and second nucleotide sequences encoding the P4H α and β subunits may be integrated into a host chromosome while the product-encoding sequences may be included on vector(s) including a CEN sequence or on a high copy number vector(s).

Preferably, the method of the invention is achieved by including the exogenous nucleotide sequences within a vector(s) including a CEN sequence. Particularly preferred are the CEN sequence-including YAC (yeast artificial chromosome) vectors (Cohen et al., 1993) and pYEUra3 vectors (Clontech, Cat. No 6195-1). Other vectors including a CEN sequence may be generated by cloning a CEN sequence into any suitable expression vector.

Where one or more of the exogenous nucleotide sequences are included in a high copy number vector(s), it is preferred that the high copy number vector(s) is/are selected from those that may be present at 20 to 500 (preferably, 400 to 500) copies per host cell. Particularly preferred high copy number vectors are the YEp vectors.

The method according to the invention enables the production of hydroxylated triple helical proteins. The term "triple helical protein" is to be understood as referring to a homo or heterotrimeric protein consisting of a polypeptide(s) or peptide(s) which include at least a region having the general peptide formula: $(Gly\ X\ Y)_n$ in which Gly is glycine, X and Y represent the same or different amino acids (the identities of which may vary from Gly X Y triplet to Gly X Y triplet) but wherein X and Y are frequently proline which in the case of Y becomes, after modification, hydroxyproline (Hyp), and n is in the range of 2 to 1500 (preferably 10 to 350), which region forms, together with the same or similar regions of two other polypeptides or peptides, a triple helical protein conformation. The term therefore encompasses natu- ral and synthetic collagens, natural and synthetic collagen fragments, and natural and synthetic collagen-like proteins (e.g macrophage scavenger receptor and lung-surfactant proteins) and as such includes any procollagen and collagen (e.g. Types I–XIX) with or without propeptides, globular domains and/or intervening non-collagenous sequences and, further, with or without native or variant amino acid sequences from human or other species. Synthetic collagen and fragments encompassed by the term "triple helical protein" may also include non-collagenous, non-triple helical domains at the amino and/or carboxy terminal ends or elsewhere.

Accordingly, product-encoding nucleotide sequence(s) suitable for use in the method according to the invention may be of great diversity. It is, however, preferred that the product-encoding nucleotide sequence(s) be selected from nucleotide sequences encoding natural collagens and fragments thereof, such as COL1A1 (D'Alessio et al., 1988; Westerhausen et al., 1991), COL1A2 (de Wet et al. 1987), COL2A1 (Cheah et al., 1985) and COL3A1 (Ala-Kokko et al. 1989) and fragments and combinations of these, and synthetic collagens and fragments thereof.

Product-encoding nucleotide sequence(s) which encode natural or collagen fragments may encode fragments which include or exclude the N-pro-peptide region, the N-telopeptide, the C-telopeptide or the C-propeptide or various combinations of these.

Product-encoding nucleotide sequences which encode synthetic collagens and fragments thereof, preferably encode a polypeptide(s) or peptide(s) of the general formula: $(A)_l$—$(B)_m$—$(Gly\ X\ Y)_n$—$(C)_o$—$(D)_p$, in which Gly is glycine, X and Y represent the same or different amino acids, the identities of which may vary from Gly X Y triplet to Gly X Y triplet but wherein Y must be $\geq$ one proline, A and D are polypeptide or peptide domains which may or may not include triple helical forming $(Gly\ X\ Y)_n$ repeating sequences, B and C are intervening sequences which do not contain triple helical forming $(Gly\ X\ Y)_n$ repeating sequences, n is in the range of 2 to 1500 (preferably, 10 to 300) and l, m, o and p are each independently selected from 0 and 1.

The product-encoding nucleotide sequence(s) may include a sequence(s) encoding a secretion signal so that the polypeptide(s) or peptide(s) expressed from the product-encoding nucleotide sequence(s) are secreted.

Expression of the product-encoding nucleotide sequence(s) may be driven by constitutive yeast promoter sequences (e.g ADH1 (Hitzeman et al, 1981; Pihlajaniemi et al., 1987), HIS3 (Mahadevan & Struhl,1990), 786 (no author given, 1996 Innovations 5, 15) and PGK1 (Tuite et al, 1982), but more preferably, by inducible yeast promoter sequences such as GAL1-10 (Goff et al 1984), GAL7 (St. John & Davis, 1981), ADH2 (Thukral et al, 1991) and CUP1 (Macreadie et al, 1989).

The first and second nucleotide sequences encoding the P4H α and β subunits can be of any animal origin although they are preferably of avian or mammalian, particularly human, origin (Helaakoski et al., 1989). It is also envisaged that the first and second nucleotide sequences may originate from different species. In addition, the second nucleotide sequence encoding the P4H β subunit may include a sequence encoding an endoplasmic reticulum (ER) retention signal (e.g. HDEL (SEQ ID NO:13), KDEL (SEQ ID NO:42) or KEEL (SEQ ID NO:43)) with or without other target signals so as to allow expression of the P4H in the ER, cytoplasm or a target organelle or, alternatively, so as to be secreted.

Expression of the first and second nucleotide sequences may be driven by constitutive or inducible yeast promoter sequences such as those mentioned above. It is believed, however, that it is advantageous to achieve expression of the α and β subunits in a co-ordinated manner using same or different promoter sequences with same induction characteristics, but preferably by the use of a bidirectional promoter sequence. Accordingly, it is preferred that the first and second nucleotide sequences be expressed by the yeast GAL1-10 bidirectional promoter sequence, although other bidirectional promoter sequences would also be suitable.

Multiple copies of the first, second and/or product-encoding nucleotide sequences may be introduced to the yeast host cell (e.g. present on a YAC vector or integrated into a host chromosone). It may be particularly advantageous to provide the product-encoding nucleotide sequence(s) in multicopy and, accordingly. it may be preferred to introduce the product-encoding nucleotide sequence(s) on a high copy number plasmid (e.g. a YEp plasmid).

The introduced first, second and product-encoding nucleotide sequences may be borne on one or more stably retained and segregated DNA molecules. Where borne on more than one DNA molecule, the DNA molecules may be a combination of host chromosome(s) and/or CEN sequence-including vector(s) in combination with high copy number vector(s). Some specific examples of yeast host cells suitable for use in the method according to the invention, are transformed with the following DNA molecules:

1. YEp-P3+pYEUra3-αβ,
2. YEp-P3+pYAC αβ
3. YEpCEN-P3+pYEUra3αβ
4. YEpCEN-P3+pYAC αβ
5. pYAC-P3+pYAC αβ
6. pYAC-P3+pYEUra3αβ
7. pYACαβ-P3;

wherein P3 represents a product-encoding nucleotide sequence(s), α and β represent, respectively, nucleotide sequences encoding the P4H α subunit and P4H β subunit, CEN represents an introduced centromere sequence. The pYEUra3 and pYAC vectors include CEN sequences.

Triple helical protein products produced in accordance with the method of the invention may be purified from the yeast host cell culture by techniques including standard chromatographic and precipitation techniques (Miller & Rhodes, 1982). For collagens, pepsin treatment and NaCl precipitation at acid and neutral pH may be used (Trelstad, 1982). Immunoaffinity chromatography can be used for constructs that contain appropriate recognition sequences, such as the Flag sequence which is recognised by an M1 or M2 monoclonal antibody, or a triple helical epitope, such as that recognised by the antibody 2G8/B1 (Glattauer et al., 1997).

Yeast host cells suitable for use in the method according to the invention may be selected from genus including, but not limited to, Saccharomyces, Kluveromyces, Schizosaccharomyces, Yarrowia and Pichia. Particularly preferred yeast host cells may be selected from *S. cerevisiae, K. lactis, S. pombe, Y. lipolytica* and *P. pastoris*.

As indicated above, it is particularly preferred that the first, second and product-encoding nucleotide sequences be introduced to the yeast host cell by transformation with one or more YAC vectors. YAC vectors are linear DNA vectors which include yeast CEN sequences, at least one autonomous replication signal (e.g. ars) usually derived from yeast, and telomere ends (again, usually derived from yeast). They also generally include a yeast selectable marker such as URA3, TRP1, LEU2, or HIS3, and in some cases, an ochre suppressor (e.g. sup4-o) which allows for red/white selection in adenine requiring strains (i.e. the mutation of the adenine gene being due to a premature ochre stop codon). More commonly, two yeast selectable markers are included, one on each arm of the artificial chromosome (each arm separated by the CEN). This allows selection of only those transformed hosts containing YACs with introduced sequences of interest within the desired restriction cloning site. That is, correct insertion of the sequences of interest (e.g. an expression cassette) rejoins the two arms of the restricted YAC, thus rendering transformants prototrophic for both markers. YACs have been designed to allow for the introduction of large exogenous nucleotide sequences (i.e. of the order of 100 kb or more) into yeast host cells. The present inventors have hereinafter shown that such YACs may be used for the stable expression of multiple exogenous nucleotide sequences (e.g. nucleotide sequences encoding a natural collagen and both the α and β subunits of P4H).

In some embodiments of the invention, it may be preferred that one or more (but not all) of the first, second and product-encoding nucleotide sequences be introduced to the yeast host cell by transformation with one or two YEp vectors. YEp vectors carry all or part of the yeast 2μ plasmid with at least the ori of replication. They also include a yeast selectable marker such as HIS3, LEU2, TRP1, URA3, CUP1 or G418 resistance, and often also contain a separate ori, generally ColE1, and markers, such as ampicillin resistance, for manipulation in *E.coli*. They show high copy number, for example 20–400 per cell, and are generally efficiently segregated. Stability during cell division is dependent on the vector also containing the REP2/STB locus from the 2μ plasmid. However, stability is not as good as endogenous 2μ plasmid of the host, particularly when heterologous genes are induced for expression. Stability also declines with increasing plasmid size. (Wiseman, 1991).

The terms "comprise", "comprises" and "comprising" as used throughout the specification are intended to refer to the inclusion of a stated component or feature or group of components or features with or without the inclusion of a further component or feature or group of components or features.

The invention will now be described by way of reference to the following non-limiting examples and accompanying figures.

BRIEF DESCRIPTION OF THE
ACCOMPANYING FIGURES

FIG. 2 shows the nucleotide sequence for the COLIII1.6 kb (DNA SEQ ID NO:39).

Figure 3:
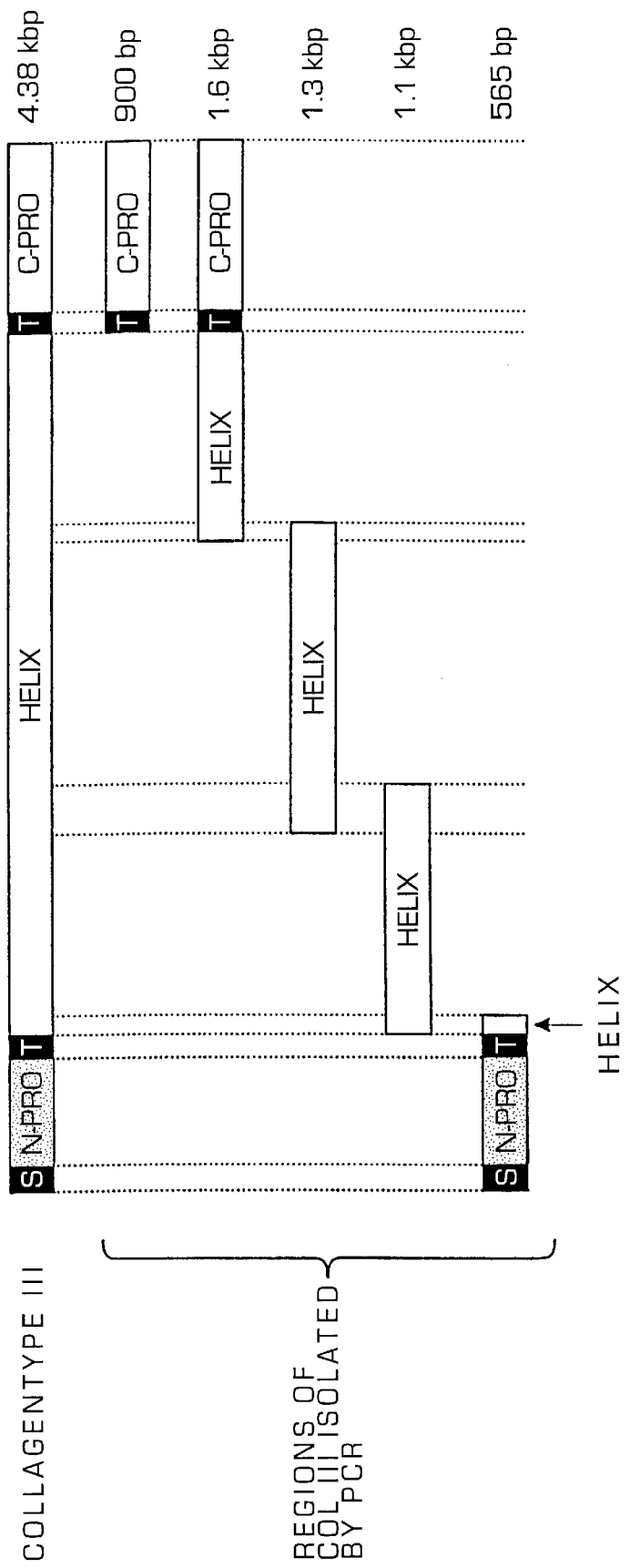

FIG. 3 shows, diagrammatically, regions of the human collagen III gene that have been isolated by PCR. The 1.6 kb DNA used in the examples hereinafter is also shown. It is to be understood that the other regions shown in the figure could substitute for the COLIII1.6 kb DNA in those examples.

Figure 4:
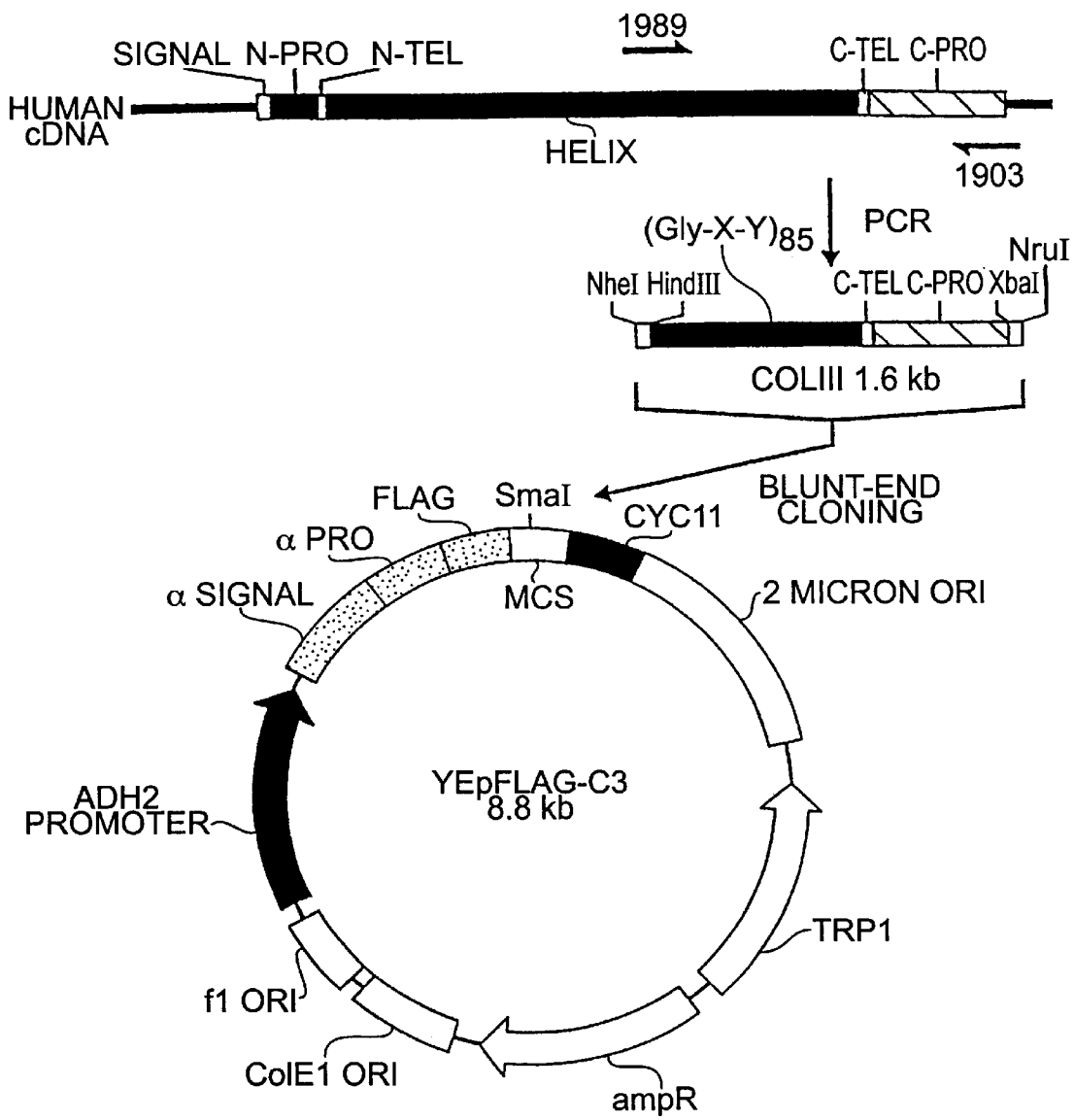

FIG. 4 shows, diagrammatically, the construction of the expression vector YEpFlagCOLIII1.6 kb (labeled YEpFlag-C3).

Figure 5:
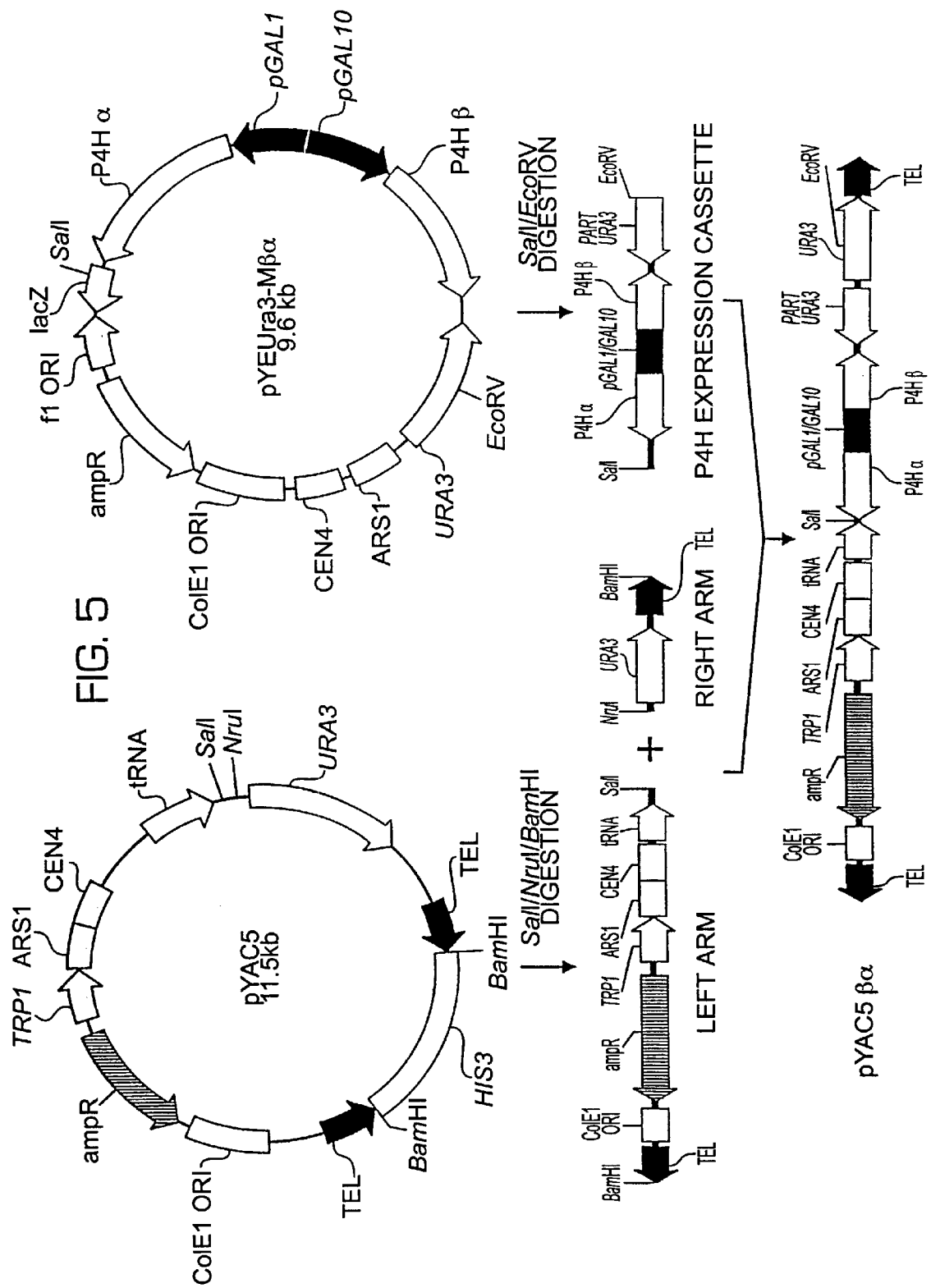

FIG. 5 shows, diagrammatically, the construction of pYAC5 βα.

Figure 6:
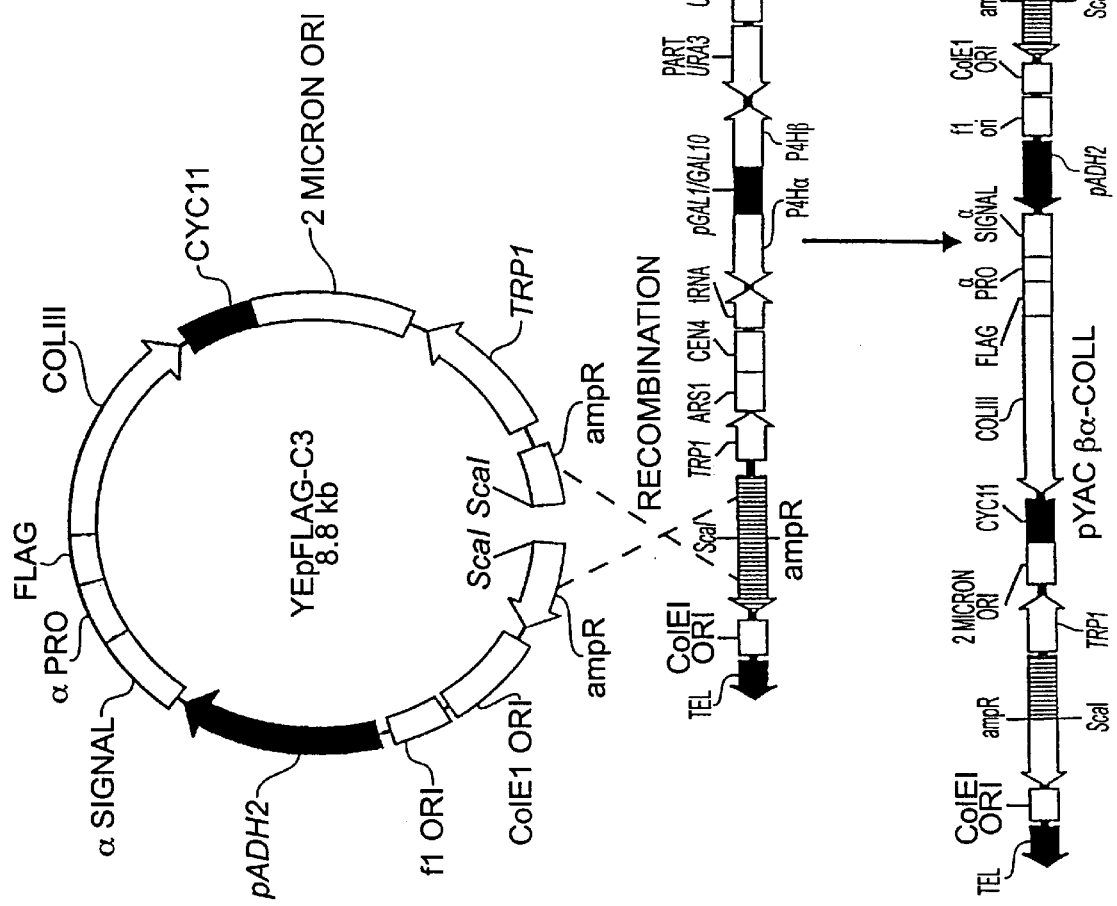

FIG. 6 shows, diagrammatically, the construction of pYAC βα-COL III1.6 kb.

Figure 7:
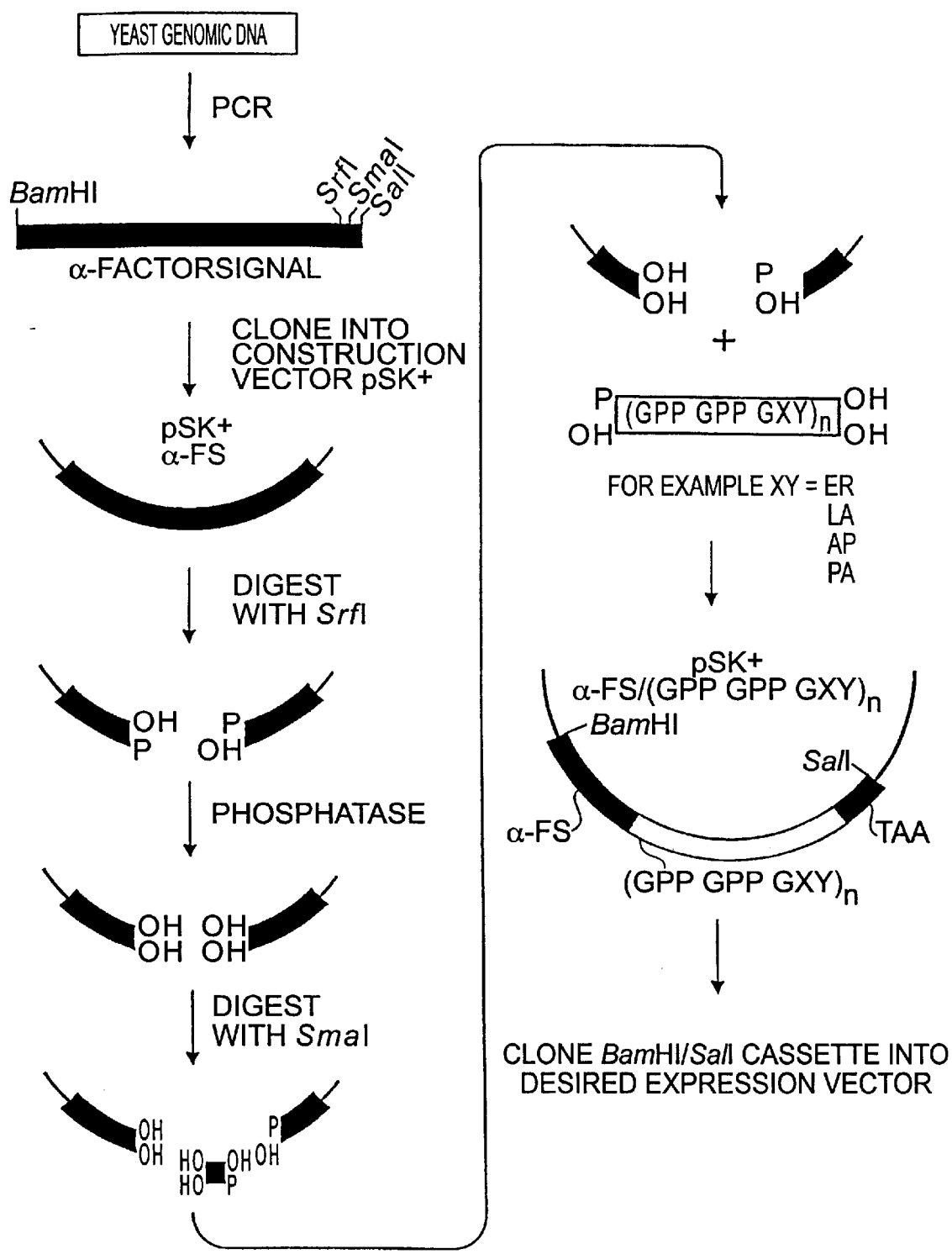

FIG. 7 outlines the construction of synthetic collagen products.

FIG. 8 provides the nucleotide sequence (SEQ ID NO:40) for SYN-C3 together with the amino acid sequence (SEQ ID NO:41) of the encoded polypeptide.

EXAMPLES

Example 1

Construction of a Yeast Vector for Co-ordinated Co-expression of the α and β Subunits of Prolyl4-hydroxylase Production of Yeast Expression Vector pYEUra3 (Clontech) contains the bidirectional promoter for GAL1-10 expression. Induction by galactose in the absence of glucose results in high level expression from pGAL1 of any protein encoded by DNA sequences inserted in the correct orientation in the MCS (multiple cloning site) [either XhoI, SalI, XbaI or BamHI sites] provided there is an initiating ATG start codon. For pGAL10, expression induced by galactose occurs if the DNA sequences to be expressed are inserted in frame with the ATG codon of GAL10 when said DNA sequences to be expressed is inserted in the EcoRI site.

In order to utilise the EcoRI site for cloning, without the necessity that the insert be in frame with the ATG of GAL10 for expression, it was necessary to modify pYEUra3 to remove the GAL10 initiation codon. This was done as follows. A PCR fragment was generated using pYEUra3 as template and primers 3465 (5'-CTG.TAG.AGG.ATC.CCCGGG.TAC.GGA.GC-3' (SEQ ID NO:1), where the BamHI site is underlined) and primer 1440 (5'TTA.TAT.TGA.ATT.CTC.AAA.AAT.TC-3' (SEQ ID NO:2), where the EcoRI restriction site is underlined). Primer 1440 introduces an EcoRI site preceding the initiating ATG of GAL10 in pYEUra3. The PCR fragment was restricted with BamHI and EcoRI and cloned into pYEUra3 similarly digested with BamHI and EcoRI, replacing the BamHI-EcoRI fragment containing an ATG start codon with a BamHI-EcoRI fragment lacking this ATG, to generate plasmid pYEUra3.2.12. The EcoRI site can then be used as a cloning site for which an initiating codon must be provided by the inserted DNA sequence as with the MCS at the other end of the promoter, thus placing it under control of the bidirectional pGAL1-10 promoter and rendering expression inducible by galactose as are DNA sequences inserted in the MCS at the other end of the promoter. Cloning DNA sequences in the MCS and in the EcoRI site allows for co-ordinate expression by the bidirectional promoter when induced by galactose.

Isolation of DNA Molecules Encoding the α and β Subunits of P4H

The α subunit of P4H was PCR amplified from cDNA (Clontech Human Kidney Quick Clone™ cDNA Cat.#7112-1) using primers 1826 (5'-TGT.AAA. ATT.AAA. GGA.TCC.CAA.AG.ATG.TGG.TAT-3', (SEQ ID NO:3), where the BamHI site is underlined, ATG is the initiating codon for the α subunit) and 1452 (5'-GCCG. GGA.TCC.TG.TCA.TTC.CAA. TGA.CAA.CGT-3' (SEQ ID NO:4), wherein the BamHI site is underlined TCA translation stop codon). Two isoforms were obtained and cloned into the BamHI site of pBluescript II SK+[Stratagene Cat.#212205] as storage vector to give pSK+α.1 (form I) and pSK+α.2 (form II). There are no BamHI sites in the DNA encoding the α subunit. The signal sequence for secretion is present in the BamHI fragment of both forms.

The β subunit of P4H [also known as PDI/protein disulfide isomerase] [Pihlajaniemi et al., 1987] was PCR amplified from cDNA (Clontech Human Kidney Quick Clone™ cDNA Cat. #7112-1) using primer pairs 2280 (5'-AC.TGG.ACG.GAT.CCC.GAG.CGC.CCC.GCC.TGC. TCC.GTG.TCC.GAC.ATG-3' (SEQ ID NO:5)) and 2261 (5'-G.GTT.CTC.CTT.GGT. BstEII site is underlined for the amino terminal part of the β subunit and primer pairs 2260 (5'-GAA.GGG.GAG.GTC.ACC.AAG.GAG.AAC-3' (SEQ ID NO:7), where the BstEII site is underlined and 1932 (5'-CC.TTC.AGG.ATC.CTA. TTA.GAC.TTC.ATC.TTT.CAAC.AGC-3' SEQ ID NO: 8)) for the carboxy terminal part of the β subunit. The two PCR fragments for the β subunit were then ligated together following BstEII digestion, to produce a single fragment encoding the entire β subunit. This fragment was then amplified using the primers 2280 (5'-AC.TGG.A CG.GAT.CCC.GAG.CGC.CCC.GCC.TGC. TCC.GTC.TCC.GAC.ATG-3' (SEQ ID NO:9), where the BamHI site is underlined, and ATG is the initiating codon for the β subunit) and primer 1932 (5'-CC.TTC.A GG.ATC.CTA.TTA.GAC.TTC.ATC.TTT.CAC. AGC-3' (SEQ ID NO:10), where the BamHI site is underlined and TTA is the translation stop codon for the β subunit) and then cloned into the BamHI site of pBluescript SKII+to generate the storage vector pSK+β. Subsequently, the BamHI fragment of pSK+β was amplified by using primers 2698 (5'-CTA.GTT.GAA.TTC. TAC.ACA.ATG.CTG.CGC.CGC.GCT.CTG.CTG-3' (SEQ ID NO:11), where the EcoRI site is underlined and ATG. is the initiating codon for the β subunit) and 2699 (5'-GCA.ATG.GAA.TTC.TTA.TTA. CAG.TTC.GTG.CAC.AGC.TTT-3' (SEQ ID NO:12), where the EcoRI site is underlined, and TTA. TTA. provides two translation stop codons, and GTG. changes a lysine [K] residue to a histidine [H] residue to provide a native yeast ER retention signal, HDEL (i.e., His.Asp.Glu.Leu (SEQ ID NO:13)) rather than a mammalian ER (KDAEL (SEQ ID NO:14)) retention signal). The resultant PCR fragment was then blunt end cloned into the SrfI site of pCRScript [Stratagene, Cat.# 211190] to generate pCRScriptβ. After retrieving the EcoRI fragment containing the β subunit from pCRScriptβ by EcoRI digestion, the fragment was again cloned into the EcoRI site of pCRScript to generate pCRScriptβEcoRI#4.

Figure 1:
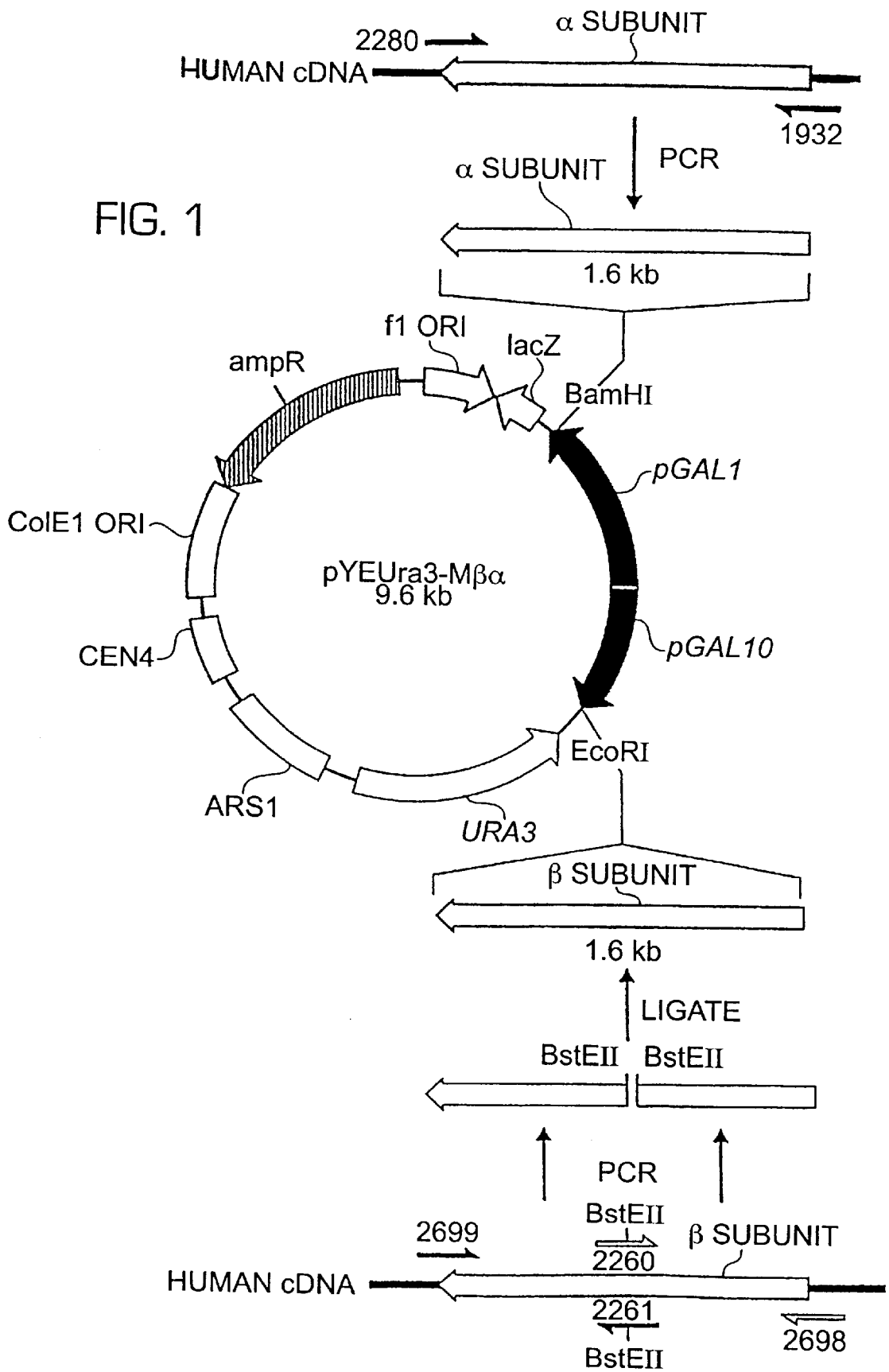
FIG. 1 shows, diagrammatically, the construction of the expression vector pYEUra3.2.12β#39α#5 (labeled pYEUra3-Mβα).

Construction of Yeast Expression Vector Including Fragment Encoding the α and β Subunit of P4H The β subunit fragment was obtained as an EcoRI fragment from EcoRI digestion of pCRScriptβEcoRI#4. This EcoRI fragment was cloned into the EcoRI site of pYEUra3.2.12 to generate plasmid pYEUra3.2.12β#39. The α subunit fragment from pSK+α.1 was re-excised from pSKα.1 by BamHI and cloned into the BamHI site of pYEUra3.2.12β#39 to give pYEUra3.2.12β#39α#5] (FIG. 1). The β subunit fragment is under control of pGAL10 and the α subunit fragment is under control of pGAL1. This is a bidirectional promoter and allows co-ordinated induced expression of both subunits of prolyl-4-hydroxylase. Both fragments provide a native ATG initiating codon for translation. The encoded β subunit has its own signal secretion signal and a HDEL endoplasmic retention (ER) sequence at the carboxy terminus of the protein. While the encoded α subunit with its own signal sequence has no ER retention signal it should, nevertheless, be retained through its interaction with the β subunit.

Example 2

Co-ordinated Co-expression of a Collagen Segment and Prolyl-4-hydroxylase (α and β Subunit) and Synthesis of Hydroxylated Collagen Type III in Yeast A 1.6 kbp recombinant collagen fragment was generated by PCR using primers 1989 (Forward primer 5'-gct.agc.aag.ctt GGA.GCT.CCA. GGC.CCA.CTT. GGG.ATT.GCT.GGG-3' (SEQ ID NO:15) and 1903 (Reverse primer 5'-tcg.cga.tct.aga.TTA. TAA.AAA.GCA. AAC.AGG.GCC.AAC.GTC.CAC. ACC-3' (SEQ ID NO:16) homologous to a region of the collagen type III alpha I chain (COL3A1). The template for isolation of the fragment of type III collagen alpha 1 chain was prepared from Wizard purified DNA obtained from a cDNA library [HL1123n Lambda Max 1 Clontech Lot#1245, Human Kidney cDNA 5'-Strectch Library].

The actual size of the isolated 1.6 kbp fragment is 1635 bp, comprising 1611 bp of COL3A1 DNA flanked either side by 12 bp derived from the primers. The 1611 bp of COL3A1 DNA corresponds to nucleotides #2713–4826 (i.e codon #905–1442) of the full-length coding sequence, thereby spanning a portion of the α-helix region, all of the C-telo-peptide, all of the C-pro-peptide and stop codon.*[1] The nucleotide sequence for the COL3A1 DNA is provided at FIG. 2. The region covered by the COL3A1 DNA is shown at FIG. 3. The 1.6 kbp fragment has a NheI (GCTAGC (SEQ ID NO:17)) site and a HindIII (AAGCTT (SEQ ID NO:18)) site added at the 5'-end and a XbaI (TCTAGA(SEQ ID NO:19)) site and a NruI (TCGCGA (SEQ ID NO:20)) site added at the 3' end [where the 5' end is taken to be the forward direction of the reading frame, ie the amino terminal end of the derived coding sequence, and the 3' end is that derived from the reverse primer corresponding to the 3' end of the gene and carboxy end of the derived amino acid sequence]. This confers portability on the collagen fragment. *[1] [Codon numbering for collagen typo III alpha 1 chain: ATG. codon #1; codon #1-codon #24, signal sequence; codon #25codon #116, N-propeptide sequence, codon #117-codon #130, N-telo-peptide sequence; codon #131-codon #1161, α-helix sequence; codon #1162codon #1186, C-telo-peptide; codon #1187codon #1441, C-pro-peptide; codon #1442, stop] and [corresponding nucleotide numbering for collagen type III alpha 1 chain: nucleotide #1–72, signal sequence; nucleotide #73–348, N-pro-peptide sequence; nucleotide #349–390, N-telo-peptide; nucleotide #391-nt#3983, α-helix region; nucleotide #3984–4058, C-telo-peptide; nucleotide #4059–4823, C-pro-peptide sequence; nucleotide #4824–4826, stop codon].

The 1.6 kbp fragment was cloned into the SmaI site of YEpFlag1 [IBI Catalogue #13400] so that the coding sequence is fused in frame with the vector expressed Flag protein. This allows for in frame expression of the introduced collagen gene fragment as a fusion protein when grown on ethanol. The blunt end cloning was performed by ligation of the SmaI digested vector sequence [gel purified] and the 1.6 kbp PCR fragment [gel purified, non-phosphorylated] at 20° C., in the presence of SmaI, to prevent recircularisation of the vector alone and reduce the level of false positive transformants obtained. There are no SmaI, NheI, HindIII, XbaI or NruI sites in the fragment of collagen DNA used in the cloning.

Small scale mini-preparations [prepared using Bio101 columns and described methods for their use] of DNA from ampicillin resistant transformant colonies of E.coli were screened by restriction enzyme analysis. 10 ml cultures rather than 1 ml cultures were required to prepare an adequate level of DNA for analysis, as YEpFlag plasmids do not appear to be at a high copy number in E. coli.

The fusion protein was of the form: yeast α factor signal sequence for direction to the ER and commitment to the yeast secretion pathway, yeast α factor propeptide with cleavage sites for kex 2-endopeptidase, resulting in removal of all α-factor amino acid residues and generation of a free Flag-tagged amino terminal end, Flag peptide for detection and tagging of the fusion protein (8 amino acid residues), linker peptide (4 amino acid residues), collagen helix (255 amino acid residues), collagen C-telopeptide [C-tel] (25 amino acid residues) and C-propeptide [C-pro] (255 amino acid residues) (for aid in formation of triple helix). The expected Flag-tagged protein consists of 547 amino acid residues with a expected MW of~60 kDa].

Expression of the fusion protein in YEpFlag1 is under the control of the ADH2 promoter which is repressed by glucose but active in the presence of ethanol [a by-product of glucose metabolism]. There are multiple copies of the vector in individual yeast transformants due to the presence of the yeast 2 micron origin of replication in the vector, which leads to elevated expression of the 1.6 kbp PCR collagen fragment when glucose repression is lifted by consumption of glucose during growth. One unique feature of this cloning scheme is that inserts of the 1.6 kbp collagen fragment in the wrong orientation will not form fusion products as the terminal leucine residue preceding the stop codon is coded by the codon AAT. In reverse orientation this generates a stop codon TAA. The result of incorrect insertion is the addition of only a single leucine coding codon [the stop codon TAA in reverse is AAT] following the Flag sequence before the protein is terminated.

The amino acid sequence of the Flag-tagged fusion protein at the point of fusion is N-Asp-Tyr-Lys-Asp-Asp-Asp-Asp-Lys-[Flag]-Ala-Ser-Lys-Leu-[linker]-Gly-Ala-Pro-Gly-Pro-Leu-Gly-Ile-Ala-[α-helix](SEQ ID NO:21).

The YEpFlag collagen construct [hereinafter referred to as YEpFlag COLIII1.6 kb; FIG. 4] was introduced into a tryptophan prototrophic yeast strain such as for example BJ3505 [a pep4::HIS3 prb-1.6R HIS3 lys2-208 trp1-101 ura3-52 gal2 can1], BJ5462 [α ura3-52 trp1 leu2-1 his3-200 pep4::HIS3 prb-1.6R can1 GAL], (YGSG) JHRY1-5Dα [α his4-519 ura3-52 leu2-3 leu2-112 trp1 pep4-3] or KRYD1 [BJ3505×BJ5462 diploid] by transformation using electroporation, lithium acetate or spheroplast regeneration. Tryptophan auxotroph transformants were obtained, grown to high cell density in selective media [lacking tryptophan] followed by transfer to YPHSM, YEPM or YEPD or YEPGal, YEPE as described in the protocol provided with the YEpFlag expression system [IBI catalogue #13400]. At 3–9 days following inoculation 1 ml aliquot's of culture were made and pellets and supernatants separated by centrifugation at 130000 rpm in a benchtop centrifuge. Total yeast pellets were resuspended in 100 μof gel loading buffer [5×SDS] containing PMSF [0.002M], vortexed vigorously for 2 minutes, and boiled for 5 minutes. From the pellets 900 μl supernatants were retained to which 100 μl 5×SDS/ 0.002M PMSF was added, and treated as described for the pellets. For both pellets and supernatants 20 μl aliquots were assayed by Western blot analysis of SDS-PAGE yeast total protein or of supernatants [media] following transfer to nitrocellulose and prehybridisation of the filters in blotto. Western blotting was carried out using α-Flag MAb M1 [against N-terminal free Flag] (International Biotechnologies Inc., (Eastman Kodak) Cat. No. IB13001) or M2 [against Flag] (International Biotechnologies Inc., (Eastman Kodak) Cat. No. IB13010).

Western blots revealed the presence of a protein band of approximately 60 kDa. This is the expected size of a protein fusion containing Flag-helix-C-tel-C-pro. After prolonged incubation the Flag responsive antibodies detected the appearance of the fusion product in the media. Detection in both pellet and media supernatant with M1 antibody demonstrates that the α factor leader has been completely removed. No precursor forms with α factor pro-region [glycosylated or not] were observed.

No band corresponding to 60 kDa was obtained which hybridised to M1 or M2 with proteins obtained from untransformed yeast hosts. When yeast transformed with YEpFlag [no insert] alone was used, bands were obtained in pellets, but only with M2 MAb. These bands correspond to un-secreted α-proregion-with C-terminal Flag and various glycosylated forms of the same. No Flag is detected in supernatants but this is to be expected as it is only 8 amino acids long. No expression from the ADH2 promoter for any construct is observed in the presence of glucose.

YEpFlagCOLIII 1.6 kb was also co-introduced [co-transformed] into yeast strains such as BJ5462 and KRDY1 which are capable of growth on galactose along with pYEUra3 [Clontech ][pYEUra3 and its derivatives contain the bidirectional GAL1-10 promoter. Both the ADH2 and GAL1-10 promoters are repressed by glucose. The GAL1-10 promoter is induced by galactose] or pYEUra3.2.12 [a modification of the Clontech parent vector which allows cloning of genes into an EcoRI site without the necessity of the introduced gene being in the correct reading frame] or pYEUra3.2.12β#39 [in which the DNA encoding the β subunit (equivalent to protein disulfide isomerase of prolyl-4-hydroxylase is cloned into the EcoRI site of pYEUra3.2.12 under control of GAL10 promoter] or pYEUra3,2.12β#39α#5 [in which the DNA encoding the α subunit of P4H is cloned into the BamHI site of pYEUra3.2.12β#39 under control of the GAL1 promoter].

Transformants were selected on media lacking tryptophan or uracil or lacking both tryptophan and uracil. As previously done with tryptophan transformants obtained above with YEpFlag or YEpFlagCOLIII1.6 kb, transformants were grown in selective media prior to growth in YPHSM, YEPM, YEPD ,YEPG or YEPE and after 4 days galactose was added to a final concentration of 2%, 0.5% or 0.2%. Total yeast protein or supernatants were analysed by Western blot analysis as described above except that a third MAb [5B5 against the β subunit] (Dako Corporation, Cat. No. M877) was also used.

Western blot analysis revealed the presence of a ~60 kDa band in trp or trp ura yeast transformed with YEpFlag COLIII1.6 kb but not YEpFlag alone when screened with MAb M1 or M2 as was previously the case with transformants obtained with single plasmid transformation.

Analysis also showed the presence of a ~60 kDa band in ura or ura trp but not trp yeast transformants transformed with pYEUra3.2.12β#39 or pYEUra3.2.12β#39α#5 or cotransformed with same plus YEpFlag or YEpFlagCOLIII 1.6 kb when screened with anti-α subunit MAb 5B5 but only following induction with galactose and only when galactose was between 0.2 and 0.5% and not at 2%. The expected size for the β subunit is also 60 kDa. This band is not detected by M1 or M2 in uracil auxotrophic yeast transformed with pYEUra3.2.12β#39 or pYEUra3.2.12β#39α#5 alone.

At the time of the experimentation, an antibody for the detection of expression of the α subunit from the bidirectional GAL1,10 pr pYEUra3.2.12β#39α#5 was not available but as the promoters for both GAL1and GAL10 are normally co-induced and under the control of the same UAS (upstream activation sequence) in yeast it was assumed that the α subunit is also transcribed and expressed where the β subunit is demonstrated to be expressed. To test this, the capacity for pYEURa3.2.12β#39α#5 YEpFlag COLIII 1.6 kb co-transformants induced with 0.2% galactose following at least 4 days growth on YPHSM to produce functional P4H was examined. Galactose was added following the clear demonstration of the expression of Flag-collagen by a positive response of yeast protein to M1 or M2 in Western blots and the absence of a response to MAb 5B5 against β subunit. Following induction with galactose [16 hrs] protein was again examined and the presence of M1 or M2 responsive bands and 5B5 responsive bands were separately demonstrated. Protein was transferred to PVDF membrane following SDS-PAGE and the membrane sliced into strips. Membrane strips containing protein from the region corresponding to the 60 kDa responsive area was subject to hydrolysis and amino acid analysis. Amino acid analysis revealed the presence of hydroxyproline in this material from co-transformants of yeast co-transformed with YEp-FlagCOLIII1.6 kb and pYEUra3.2.12β#39α#5 after induction with 0.2% galactose but no hydroxyproline was detected with protein from control samples with or without galactose.

The media used contains peptone derived from bovine protein hydrolysates but no hydroxyproline was found in total yeast grown on this media nor in any of the singly transformed yeast [one vector alone]. Only in yeast co-transformants was hydroxyproline detected in the 60 kDa bands and then only when galactose was added. Uninduced co-transformants [no galactose] in which Flag detected collagen was expressed did not contain any hydroxyproline in the 60 kDa band excised from PVDF following transfer. Hydroxyproline was only found in the 60 kDa region and not in other regions of the blot.

The clear evidence then, is that following galactose induction of pEUra3.2.12β#39α#5 a product is produced in yeast which is capable of hydroxylating the proline residues of a co-expressed Flag-tagged collagen fragment. Such activity is not found in yeast untransformed or transformed with pYEUra3.2.12β#39 [no α subunit] or in uninduced yeast grown on ethanol or glucose.

A clear advantage of this method of co-expression for the production of hydroxylated collagen in yeast is the coordinated expression of the three genes that is possible in co-transformants. Another advantage is that the α and β subunits themselves are coordinately expressed. A third advantage is that the αβ expression vector (i.e. pEUra3.2.12β#39a#5) contains a centromere sequence and behaves as a mini-chromosome. It is therefore very stable and does not require selection pressure to be maintained for its stability. The removal of selection pressure in yeast does not appear to effect the stability of the YEpFlag collagen construct as it is in very high copy number, but clearly the ability to only be concerned with maintenance of a single plasmid in the absence of selection pressure is important rather than balancing the effects of selection pressure on the stability of three separate plasmids if the α, β and collagen fragments were separately cloned on multicopy vectors. Also the use of a bidirectional promoter to express the α and β subunits simultaneously is of benefit rather than expressing them from different promoters on different plasmids in different amounts. The α subunit probably requires the synthesis of equal or higher levels of the β subunit for its correct assembly into functional P4H ($\alpha_2\beta_2$) enzyme and co-ordinated expression appears to be an efficient mechanism to ensure this.

Example 3

Use of Yeast Artificial Chromosomes [YACs] for Co-ordinated Expression of the α and β Subunits of Prolyl-4-hydroxylase [P4H]

pYAC5 [11454 bp] (Kuhn and Ludwig, 1994) was digested with BamHI to liberate the HIS3 gene [1210 bp]

from between the 2 telomere ends and with SalI-NruI to produce two fragments [left arm: fragment 1, 5448 bp & right arm: fragment2, 4238 bp] which were gel purified. Fragment 1 was BamHI-telomere end-*E.coli* ori-β-lactamase gene [ampicillin-resistance]-TRP1-ARS1-CEN4-tRNAsup-o-SalI. Fragment 2 was BamHI-telomere end-URA3-NruI.

pYEUra3.2.12β#39α#5 was digested with SalI-EcoRV to produce a P4H expression cassette fragment of the form SalI-XbaI-BamHI-α-ATG-BamHI-pGAL1-10-EcoRI-ATG-β-EcoRI-SmaI-EcoRV [4864 bp] which was gel purified. The expression cassette fragment encoding the α and β subunits of P4H under the control of a galactose inducible bidirectional promoter was ligated with fragments 1 and 2 of the BamHI-SalI-NruI digested pYAC5 and the ligation mix used to transform the following yeast strains: BJ2407 [a/α prb1-11222/prb1-1122 prc1-407/prc1-407 pep4-3/pep4-3 leu2/leu2 trp1/trp1 ura3-52/ura3-52 ], KRYD1 [a/α ura3-52/ura3-52 trp1-Δ101/trp1 lys2-208/LYS2HIS3/his3Δ200 gal2/GAL2 can1/can1 pep4::HIS3/pep4::HIS3 prb1Δ1.6R/prbΔ1.6R], GY1 [αleu2 ade1 trp1 ura3 ], JHRY1-5Dα [αhis4-519 ura3-52 leu2-3 leu2-112 trp1 pep4-3 ], and YPH150[α/a ura3-52/ura3-52 lys2-801a/lys2-801a ade1-101o/ade1-101o leu2Δ1/leu2Δ1 trp1Δ63/trp1-Δ63 his3Δ200/his3Δ200 ] using the method for lithium acetate transformation. Yeast strains were also transformed with pYAC5 digested with BamHI and undigested pYAC5.

Ura$^+$ Trp$^+$ co-transformants were obtained for all strains where the two fragments of pYAC5 each carrying either TRP1 [SalI-CEN4-TRP1-BamHI] [fragment 1] or URA3 [NruI-URA3-BamHI] [fragment 2] as the selectable marker for transformation each on one arm of the YAC, had been linked together by the insertion of the P4H expression cassette into the SalI-EcoRV sites. This vector was designated pYAC5βα (FIG. 5). The vector was of the form BamHI-telomere-URA3-NruI/EcoRV [both sites destroyed]-β-ATG-pGAL10-1-ATG-α-SalI-tRNAsup-CEN4-ARS1-TRP1-AMPr-ori-telomere-BamHI. The presence of the CEN4 sequence means the vector behaves as a stable chromosome during replication and is segregated at least 1 copy per cell at mitosis and meiosis [as was the case for pYEUra3.2.12β#39α#5]. The telomere ends mean that the vector is linear and stable.

Transformants and controls [pYAC5 alone (circular), pYAC5 linearised by BamHI digestion] were replica plated onto nitrocellulose filters laid over selective media [SD Complete lacking uracil and tryptophan] or rich media [YEpD] and incubated 2–5 days at 30 C. till confluent. Filters were transferred to selective media containing galactose [2%] instead of glucose or rich media containing galactose [2%] as well as glucose media plates and grown at 30 C. for periods between 2 h–72 h. At the end of incubation colonies were lysed on 0.1%SDS-0.2N NaOH-0.1% β-mercaptoethanol, washed with water and filters blocked with Blotto. Production of the α and β subunits of P4H was ascertained by hybridising the treated filters with MAbs specific for the α [MAb 9-47H10] (ICN Biomedical Inc. Cat. No. 631633) and β [MAb 5B5] subunits. Colonies transformed with pYAC5βα and induced with galactose showed hybridisation with MAbs against the subunits of P4H demonstrating co-ordinated production of α and β from the bi-directional GAL 1-10 promoter. Controls filters and control yeast did not produce a response to P4H MAbs. Yeast transformants carrying pYAC5βα grown on glucose [a repressor of the bidirectional GAL 1-10 promoter] also did not produce a positive response.

Positive transformants identified in the above screening procedure were precultured/grown in 10 ml liquid culture media containing selective media lacking ura and trp or rich media [containing glucose, glycerol or raffinose]. Aliquots were transferred to inducing media [selective or rich] containing 0.2-2% galactose. Where glucose was the carbon source pellets were washed in sterile water prior to induction. After 2–20 h further growth at 30 C. cell pellets were collected, suspended in loading buffer and total yeast protein separated on SDS-PAGE and western blotted. Filters were blocked with blotto and hybridised with MAbs against both of the P4H subunits. Only those yeast transformants carrying pYAC5βα and induced with galactose gave the expected 60 kDa bands for α and β subunits. This demonstrates that the P4H expression cassette has been functionally inserted into pYAC5. The advantage of having the P4H cassette in the pYAC is twofold; [1] as with the case of pYEUra3.2.12β#39α#5 the presence of the CEN sequence means that the vector is stably maintained in this system when selection pressure is removed for growth in rich media, which increases yield through increased cell density, and [2] the pYAC5βα construct allows for the subsequent insertion of multiple and different triple helical protein expression cassettes.

Example 4

Co-expression of Collagen/triple Helical Protein Fragment(s) Expressed on a Multicopy Plasmid and P4H Subunits in Yeast Transformants Carrying pYAC5βα.

Yeast host strains containing pYAC5βα or pYAC5 were transformed with YEpFlagColIII 1.6 kb or YEpFlag alone. The form of the collagen bearing vector was circular and multicopy. In this instance, as the YEpFlagCOLIII 1.6 kb and the pYAC constructs both contain the same selectable marker, yeast transformants producing Flag tagged-collagen were identified by colony hybridsation with MAbs against Flag [M1 or M2]. Colonies were also screened for whether they carried extra copies of bla gene [multicopy] by identifying those colonies producing increased levels of β-lactamase by PADAC assay (Macreadie et al., 1994). In other examples, the multicopy plasmid could utilise a different selectable marker other than URA3 or TRP1 found on each arm of the YAC. Various co-transformant types carrying pYAC5βα and YEpFlag COLIII 1.6 kb were assayed as in Example 1 for collagen production, P4H subunit production, and P4H activity. Those co-transformants containing pYAC5βα plus YEpFlag COLIII 1.6 kb were then screened as described in the previous example for hydroxylated collagen to identify 60 kDa bands in western blots responding to MAbs against the α and β and Flag following induction. The α and β subunits were only identified following galactose induction. Hydroxylated protein was only identified following induction of both the α and β subunits of P4H.

Example 5

Introduction of Collagen Expression Cassette Into pYAC5 and pYAC5βα

YEpFlag was linearised by digestion with ScaI which cuts at a single recognition site in the ampicillin resistance gene for β-lactamase [bla]. There are no ScaI sites in the 1.6 kb collagen fragment insert so ScaI could also be used to linearise YEpFlagColIII 1.6 kb. Linear DNA was used to transform yeast containing pYAC5 or pYAC5βα.Yeast transformants producing Flag tagged-collagen were identified by colony hybridsation with MAbs against Flag [M1 or M2]. Colonies carrying extra copies of bla gene [multicopy] were also identified. Those colonies producing increased levels of β-lactamase by the PEDAC assay were found to have inserted a copy of YEpFlag COLIII 1.6 kb into the pYAC5 or pYAC5βα vector of the host strain and correspond to those colonies positive to MAbs M1 or M2. The increased β-lactamase activity is a result of gene amplification resulting from homologous recombination between the linearised bla gene on YEpFlagCOLIII 1.6 kb and the bla gene on pYAC. The new plasmids formed by insertion into pYAC5 or pYAC5βα of the YEpFlag COLIII 1.6 kb vector were designated pYAC-COLIII 1.6 kb and pYAC αβ-COLIII 1.6 kb (FIG. 6). Expression experiments were performed and only those strains carrying all 3 genes on the YAC [pYAC βα-COLIII 1.6 kb] and induced for P4H with galactose produced hydroxylated collagen.

Example 6

Cloning and Expression of a Synthetic Collagen Protein

A strategy is described for the generation of "synthetic/novel" collagen proteins involving the in vitro assembly of synthetic oligonucleotides repeat sequences encoding the peptides GPP.GPP.GLA (SEQ ID NO:22), GPP.GPP.GER (SEQ ID NO:23), GPP.GPP.GPA (SEQ ID NO:24) or GPP.GPP.GAP (SEQ ID NO:25). The synthetic collagen sequences are engineered to contain a high percentage of proline residues as this residue has been shown to confer thermal stability to collagen molecules, The residue pairs chosen in the above peptides for the XY position (i.e. LA, ER, PA or AP), are selected since they appear in statistically higher amounts in fibrillar collagens.

Mixtures of synthetic oligonucleotides encoding SEQ ID NO:22, 23, 24 or 25 may be joined together to generate DNA fragments of discrete lengths, encoding synthetic collagen proteins of discrete molecular size and with different physical characteristics. These synthetic gene segments can be cloned into various expression vectors for subsequent production of a collagen product in yeast. An outline of the strategy for construction of a synthetic oligonucleotide encoding a collagen is shown in FIG. 7 where XY is shown, for the purposes of exemplification only, as ER, LA, AP, PA.

Such synthetic oligonucleotides have been synthesised and several libraries containing gene segments of various lengths have been generated by ligating these oligonucleotides together (maximum visible DNA length approx. 1000 base pairs coding for a polypeptide of ~350 amino acid residues).

Example 7

Construction of a Synthetic Hydroxylated Triple Helical Protein for Stable Expression in Yeast A region of Type III collagen was selected for its known capacity to bind and activate platelets (through an integrin binding site near -gla-Leu)Ala-Gly-Ala-Pro-Gly-Leu-Arg (SEQ ID NO:26)). A region of 5 GLY-X-Y repeats to the N-terminal side and 7 GLY-X-Y repeats to the C-terminal side were also included to form the basic repeat unit for inclusion in the synthetic fragment. The sequence of the repeat was GGKGDAGAPGERGPP-GLAGAPGLR-GGAGPPGPEGGKGAAGPPGPP (SEQ ID NO:27). This corresponds to residues 637–681 (nucleotides 1909–2043) in the COL3A1 gene [with Met=1]. At the 5'-end of the DNA an EcoRI site and NheI site was included such that the NheI site provided an initiating methionine. Thus the sequence at the amino end is MGAPGAP (SEQ ID NO:28), where GAPAP (SEQ ID NO:29) is the natural sequence flanking the repeat in COL3A1. The repeat was linked to a second repeat by a linker which introduced a Bsp120I site for later manipulations and provided the sequence GGP between the first and second repeat unit. The second repeat was linked to a third repeat by a linker which introduced a BssHII site [again for later manipulation] and resulted in the amino acid sequence GAR. The third repeat was flanked by 2 additional GPP triplets, a GCC triplet and finally GLEGPRG (SEQ ID NO:30). This was a result of including coding sequence that provided for XhoI, SacII and NheI sites. These were included for flexibility of cloning at later stages. The NheI site provides an in frame stop codon.

The synthetic fragment was produced by PCR from primers against COL3A1 in 3 pieces initially. Fragment 1 was EcoRI-NheI-Met-[GAP]2-[REPEAT]1-Bsp120I. The primers for this were 5'-aattccatg-(SEQ ID NO:31) [up] [primer U101] and 5'-ggcc-acctggtggacctggtgg-3' (SEQ ID NO:32) [down] [primer D101]. The second PCR fragment used primers 5'-ggccc-ggtggtaagggtgacgc-3' (SEQ ID NO:33[up][ primer U102] and 5'-cgcgc-acctggtggacctgg-3' (SEQ ID NO:34) [down] [primer D102]. For the 3rd repeat primer pairs used were 5'-cgcgc-ggtggtaagggtgacgctgg-3' (SEQ ID NO:35) [up] [primer U103] and 5'-acaaccctggtggacctggtggacc-tggtggacctgggtgg-3'(SEQ ID NO:36) [down] [primer D103]. The three fragments form the PCR reactions were gel purified and ligated together. The DNA from the ligation mixture was then used as the template for a further round of PCR using primer U101 and a new primer at the 3' end [5'-ctagccccgcggaccctcgagaccaca-acaaccctggtgg-3' (SEQ ID NO:37) ] [down] [primer D104]. A band of approximately 500 bp was produced and gel purified, digested with EcoRI-NheI and ligated to pYX141 (Ingenous Cat. No MBV-025-10) [LEU2-CEN-p786] also digested with EcoRI-NheI before being transformed into E.coli. Transformants were screened by PCR using primers for the second fragment and DNA from positive colonies were miniprepped and screened by enzyme digestion with EcoRI-NheI for the presence of an insert of approximate 500 bp. This storage vector was designated pYX-SYN-C3-1. The EcoRI-NheI fragment was transferred to pYX243 [2u-LEU2-pGAL] (Ingenous Cat. No MBV-035-10) to give pYX-SYN-C3-2 and this plasmid was introduced into a yeast host cell including nucleotide sequence for the carrying the P4H α and β subunits [either pYEUra3.2.12β#39α#5 or pYACαβ]. Expression following galactose induction was determined by using a MAb 2G8/B1 (Werkmeister & Ramshaw, 1991) which recognises the sequence GLA-GAPGLR (SEQ ID NO:38). An EcoRI-SacII fragment from pYX-SYN-C3-2 was also introduced into the EcoRI-SacII of YEpFlag to produce YEpFlag-SYN-C3 and this too was introduced into a yeast host cell expressing P4H on induction by galactose. A product of approximately 18 kDa [the expected size of SYN-C3] was detected in yeast induced with galactose by Western blotting.

The nucleotide sequence for SYN-C3 is provided at FIG. 8 together with the amino acid sequence of the encoded product.

Example 8

The Use of Yeast Other Than *Saccharomyces cerevisiae*

The GAL1-10 promoter is functional in Kluyveromyces whilst the ADH2 promoter is constitutively expressed in S.

pombe. By shifting the expression cassettes to appropriate vectors, other yeast hosts can be used. K. lactis for instance has been shown in some instances to display less proteolytic activity for recombinant products. Alternatively, P. pastoris could be used for multiple integration of the expression cassette for αβ into the chromosome.

For expression in P. pastoris, the nucleotide sequence described in the previous example encoding the synthetic triple helical protein [SYN-C3] was inserted into the P. pastoris vector pPIC9 (Invitrogen, Cat. No. K1710-01) at the EcoRI-NotI sites [pPIC-SYN-C3]. Following digestion with either BglII or SalI, the plasmid was introduced into P.pastoris where it was integrated at either the AOX1 or HIS4 sites for BglII or SalI respectively. The nucleotide sequences encoding the P4H α and β subunits were also introduced into P.pastoris using the EcoRI site of pHIL-D2 (Invitrogen, Cat. No. K1710-01) for the β subunit and integration at HIS4 and the BamHI site of pHIL-S1 (Invitrogen, Cat. No. K1710-01) for the α subunit and subsequent integration HIS4. All three expression cassettes were under the control of the AOX1 promoter and induced by methanol.

Example 9

Enhanced Expression of Proly4-hydroxylase α and β subunits from the GAL1-10 promoter by use of Yeast with Different Backgrounds for control of Galactose Induced Expression The plasmid pYEUra3.2.12β#39α#5 [encoding the α and β subunits of P4H under the control of the GAL1-10 bidirectional promoter] can be introduced into a yeast host cell with the following genotype: a or α, ura3 trp1 egd1 btt1. In these cells, the absence of the products for the EGD1 and BTT1 genes results in higher levels of galactose induced expression from GAL4 dependent promoters such as GAL2, GAL4, GAL7, GAL1-10, MEL1 (Hu & Ronne, 1994).

Another mechanism for enhanced expression is the use of a yeast host cell carrying multiple copies of the GAL4 (Johnston & Hopper, 1982) positive transcriptional activator under its own controlled induction by galactose. This leads to enhanced expression as there is no limit to the availability of the transcriptional activator for the GAL1-10 promoter. Similarly, the yeast host cell could contain multiple copies of the SGE1 gene (Amakasu et al., 1993) which also leads to enhanced transcription from galactose induced promoters.

Various combinations of these backgrounds could also be utilised; that is egd1 btt1 SGE1$^{mc}$ or egd1 btt1 GAL4$^{mc}$ or egd1 btt1 SGE1$^{mc}$ GAL4$^{mc}$ [where mc represents multiple copies].

Example 10

Expression of Collagen From Promoters Other Than ADH2

The collagen encoding nucleotide sequence in YEpFlag COL 1.6 kb can be excised as a NheI or HindIII- XbaI or NruI fragment for insertion into other fusion vectors under the control of other promoters. Alternatively, the pADH2-α signal-A-proregion-Flag collagen cassette can be excised as a NaeI or SacI-BglII or XbaI or SpeI or SnaBI or NotI, for example, and introduced into an appropriate vector such as YEplac181 (Gietz & Sugino, 1988) or pMH158 (Heutespreute et al., 1985) for expression in different copy numbers and host backgrounds or into vectors with CEN sequences. Alternatively, CEN sequences can be introduced into the YEpFlag vector itself. The cassette can also be removed without the ADH2 promoter using NruI and introduced into an appropriate vector behind an appropriate promoter.

Collagen encoding nucleotide sequences can be expressed using the CUP1 promoter in vectors such as pYELC5 (Macreadie et al., 1989) as an alternative to the ADH2 promoter. This promoter is induced by addition of copper (i.e. copper sulfate) and may have the advantage of an increased reducing environment and enhancement of P4H activity during co-expression. A second promoter that can be used is the TIP1 promoter which is induced by cold shock. Here the stability of the expressed collagen may be enhanced without the need for hydroxylation by inducing expression by shifting growing yeast from 30° C. to 18° C.

The method according to the invention provides for the stable expression of triple helical proteins from yeast host cells. The products of the method may be natural and synthetic collagens, natural and synthetic collagen fragments and natural and synthetic collagen-like proteins. Synthetic products may show enhanced or novel functions (e.g. inclusion of RGD and/or YIGSR sequences from fibrorectin and laminin). The products may be used in a wide range of applications including bioimplant production, soft and hard tissue augmentation, wound/burn dressings, sphincter augmentation for urinary incontinence and gastric reflux, periodontal disease, vascular grafts, drug delivery systems, cell delivery systems for natural factors and as conduits in nerve regeneration.

REFERENCES

Ala-Kokko, L. et al. (1989) Biochem J. 260, 509–516
Amakasu, H. et al. (1993) Genetics 134, 675–683
D'Alessio, M. et al. (1988) Gene 67, 105–115
de Wet, W. et al. (1987) J. Biol. Chem. 262, 16032–16036.
Cheah, K. S. E. et al. (1985) Proc. Natl. Acad. Sci. USA 82, 2555–2559
Cohen D et al., (1993) Nature 366, 698–701
Gietz, R. D. & Sugino, A. (1988) Gene 74, 527–534
Glattauer, V. et al. (1997) Biochem. J. 323, 45–49.
Goff, G. et al. (1984) Gene 25, 179–188
Helaakoski, T. et al. (1989) Proc. Natl. Acad. Sci. USA 86, 4392–4396
Heuterspreute, M. et al. (1985) Gene 34, 363–366
Hitzeman, R. A. et al (1981) Nature 293, 717–722
Hu, G. Z. & Ronne, H. (1994) Nucleic Acid Res. 22, 2740–2743.
Johnston, S. A. & Hopper, J. E. (1982) Proc. Natl. Acad. Sci. USA 79, 6971–6975.
Kuhn R M & Ludwig R A, (1994) Gene 141, 125–127.
Larin Z et al., (1996) Nucleic Acid Research 24 No. 21, 4192–4196.
Macreadie, I. G. et al (1989) Plasmid 21, 147–150
Macreadie, I. G. et al. (1994) Biotechnol. Applied Biochem. 19, 265–269
Mahadevan, S. & Struhl, K. (1990) Mol. Cell Biol. 10, 4447–4455, 786
Miller, E. J. & Rhodes, R. K. (1982) Meth. Enzymol. 82, 33–64.
Pihlajaniemi, T. et al., (1987) EMBO J 6, 643–649.
St. John, T. P. & Davis R. W. (1981) J. Mol. Biol. 152, 285–316
Thukral, S. K. et al (1991) Mol. Cell Biol. 11, 699–704
Trelstad, R. L. (1982) Native collagen fractionation. In, Immunochemistry of the Extracellular Matrix Vol. 1 (H. Furthmayr, ed.) CRC Press, 31–41.
Tuite, M. F. et al (1982) EMBO J. 1, 603–608.

Westerhausen, A et al. (1991) Matrix 11, 375–379

Werkmeister, J. A. & Ramshaw, J. A. M. (1991) Biochem. J., 274, 895–898.

Wiseman, A. (1991) Genetically engineered proteins and enzymes from yeast: production control. Ellis Horwood, New York.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for producing, in yeast, a hydroxylated triple helical protein, said method comprising the steps of:
   (A) introducing into a suitable yeast host cell:
   (i) a first DNA molecule comprising a DNA sequence encoding prolyl 4-hydroxylase α-subunit (P4Hα) operably linked to a promoter functional in said yeast host cell,
   (ii) a second DNA molecule comprising a DNA sequence encoding prolyl 4-hydroxylase β-subunit (P4Hβ) operably linked to a promoter functional in said yeast host cell, and
   (iii) a third DNA molecule comprising a DNA sequence encoding a polypeptide or peptide operably linked to a promoter functional in said yeast host cell, wherein said polypeptide or peptide is one which, when hydroxylated, forms said hydroxylated triple helical protein, and wherein said polypeptide or peptide is a synthetic polypeptide or peptide represented by the following formula:

$(A)_l—(B)_m—(GlyXY)_n—(C)_o—(D)_p$, wherein GlyXY represents a triple helical forming repeating sequence,
   wherein Gly represents glycine,
   wherein X and Y, which may be the same or different, each represent an amino acid, and wherein the identity of each amino acid represented by X and Y may vary from GlyXY triplet to GlyXY triplet, but wherein at least one Y in the triple helical forming repeating sequence $(GlyXY)_n$ is proline,
   wherein A and D each represent a polypeptide or peptide domain which comprises a triple helical forming repeating sequence $(GlyXY)_n$,
   wherein B and C each represent a polypeptide or peptide domain which is heterologous to collagen proteins and which does not comprise a triple helical forming repeating sequence $(GlyXY)_n$,
   wherein n is an integer of from 2 to 1500,
   wherein each of l, m, o and p are selected from 0 and 1, with the proviso that at least one of m and o is 1, and when m is 1 and o is 0, l must be 1, and when o is 1 and m is 0, then p must be 1, and
   (B) culturing the resulting yeast host cell of step (A) under conditions suitable to express said P4Hα, said P4Hβ and said polypeptide or peptide, to produce said hydroxylated triple helical protein,
   wherein during culturing in step (B), each of said first DNA molecule, said second DNA molecule and said third DNA molecule are replicated, stably retained and segregated by the yeast host cell.

2. The method of claim 1, wherein expression of said P4Hα and said P4Hβ is controlled in a coordinated manner by a bidirectional promoter.

3. The method according to claim 1, wherein said P4Hα is an avian P4Hα or a mammalian P4Hα, and said P4Hβ is an avian P4Hβ or a mammalian P4Hβ.

4. The method according to claim 1, wherein each of said first DNA molecule, said second DNA molecule and said third DNA molecule further comprise a DNA sequence encoding a secretion signal such that P4H and said polypeptide or peptide are expressed and secreted by said yeast host cell.

5. The method according to claim 1, wherein in step (A) each of said first DNA molecule, said second DNA molecule and said third DNA molecule is present on the same vector, or on different vectors, and wherein said vector or vectors comprise a centromere (CEN) sequence.

6. The method according to claim 1, wherein in step (A), at least one of said first DNA molecule, said second DNA molecule and said third DNA molecule is present on the same vector and said vector comprises a CEN sequence, and at least one of said first DNA molecule, said second DNA molecule and said third DNA molecule is present on a high copy number vector, which may be the same vector or different vectors.

7. The method according to claim 1, wherein said yeast host cell is a member of a genus selected from the group consisting of Kluveromyces, Saccharomyces, Schizosaccharomyces, Yarrowia and Pichia.

8. The method according to claim 1, wherein the triple helical forming repeating sequence $(GlyXY)_n$ includes at least one integrin binding site.

9. The method according to claim 1, wherein said bidirectional promoter is yeast GAL-1–10 bidirectional promoter.

10. The method according to claim 3, wherein said mammalian P4Hα is human P4Hα, and said mammalian P4Hβ is human P4Hβ.

11. The method according to claim 5, wherein said vector which comprises a CEN sequence is a YAC vector.

12. The method according to claim 6, wherein said vector which comprises a CEN sequence is a YAC vector.

13. The method according to claim 6, wherein said high copy number vector is a Yep plasmid.

14. The method according to claim 8, wherein the integrin binding site comprises the amino acid sequence: GLA-GAPGLR (SEQ ID NO:38).

15. The method according to claim 11, wherein said first DNA molecule, said second DNA molecule and said third DNA molecule are present on the same YAC vector.

16. A yeast host cell which produces a hydroxylated triple helical protein upon culturing, wherein said yeast host cell comprises:
   (A) a first DNA molecule comprising a DNA sequence encoding prolyl 4-hydroxylase α-subunit (P4Hα) operably linked to a promoter functional in said yeast host cell, (B) a second DNA molecule comprising a DNA sequence encoding prolyl 4-hydroxylase β-subunit (P4Hβ) operably linked to a promoter functional in said yeast host cell, and (C) a third DNA molecule comprising a DNA sequence encoding a polypeptide or peptide operably linked to a promoter functional in said yeast host cell, wherein said polypeptide or peptide is one which, when hydroxylated, forms said hydroxylated triple helical protein, and wherein said polypeptide or peptide is a synthetic polypeptide or peptide represented by the following formula:

$(A)_l$—$(B)_m$—$(GlyXY)_n$—$(C)_o$—$(D)_p$, wherein GlyXY represents a triple helical forming repeating sequence, wherein Gly represents glycine, wherein X and Y, which may be the same or different, each represent an amino acid, and wherein the identity of each amino acid represented by X and Y may vary from GlyXY triplet to GlyXY triplet, but wherein at least one Y in the triple helical forming repeating sequence $(GlyXY)_n$ is proline, wherein A and D each represent a polypeptide or peptide domain which comprises a triple helical forming repeating sequence $(GlyXY)_n$, wherein B and C each represent a polypeptide or peptide domain which is heterologous to collagen proteins and which does not comprise a triple helical forming repeating sequence $(GlyXY)_n$, wherein n is an integer of from 2 to 1500, wherein each of l, m, o and p are selected from 0 and 1, with the proviso that at least one of m and o is 1, and when m is 1 and o is 0, l must be 1, and when o is 1 and m is 0, then p must be 1, and wherein upon culturing of said yeast host cell, each of said first DNA molecule, said second DNA molecule and said third DNA molecule are replicated, stably retained and segregated by said yeast host cell.

17. The yeast host cell of claim 16, wherein expression of said P4Hα and said P4Hβ is controlled in a coordinated manner by a bidirectional promoter.

18. The yeast host cell according to claim 16, wherein said P4Hα is an avian P4Hα or a mammalian P4Hα, and said P4Hβ is an avian P4Hβ or a mammalian P4Hβ.

19. The yeast host cell according to claim 16, wherein each of said first DNA molecule, said second DNA molecule and said third DNA molecule further comprise a DNA sequence encoding a secretion signal such that P4H and said polypeptide or peptide are expressed and secreted by said yeast host cell.

20. The yeast host cell according to claim 16, wherein in step (A) each of said first DNA molecule, said second DNA molecule and said third DNA molecule is present on the same vector, or on different vectors, wherein said vector or vectors comprise a centromere (CEN) sequence.

21. The yeast host cell according to claim 16, wherein in step (A), at least one of said first DNA molecule, said second DNA molecule and said third DNA molecule is present on the same vector and said vector comprises a CEN sequence, and at least one of said first DNA molecule, said second DNA molecule and said third DNA molecule is present on a high copy number vector, which may be the same vector or different vectors.

22. The yeast host cell according to claim 16, wherein said yeast host cell is a member of a genus selected from the group consisting of Kluveromyces, Saccharomyces, Schizosaccharomyces, Yarrowia and Pichia.

23. The yeast host cell according to claim 16, wherein the triple helical forming repeating sequence $(GlyXY)_n$ includes at least one integrin binding site.

24. The yeast host cell according to claim 17, wherein said bidirectional promoter is yeast GAL1-10 bidirectional promoter.

25. The yeast host cell according to claim 18, wherein said mammalian P4Hα is human P4Hα, and said mammalian P4Hβ is human P4Hβ.

26. The yeast host cell according to claim 20, wherein said vector which comprises a CEN sequence is a YAC vector.

27. The yeast host cell according to claim 21, wherein said vector which comprises a CEN sequence is a YAC vector.

28. The yeast host cell according to claim 21, wherein said high copy number vector is a Yep plasmid.

29. The yeast host cell according to claim 23, wherein the integrin binding site comprises the amino acid sequence: GLAGAPGLR (SEQ ID NO:38).

30. The yeast host cell according to claim 26, wherein said first DNA molecule, said second DNA molecule and said third DNA molecule are present on the same YAC vector.

31. A method for producing, in yeast, a hydroxylated triple helical protein, said method comprising the steps of:

(A) introducing into a suitable yeast host cell:

(i) a first DNA molecule comprising a DNA sequence encoding prolyl 4-hydroxylase α-subunit (P4Hα) operably linked to a promoter functional in said yeast host cell, (ii) a second DNA molecule comprising a DNA sequence encoding prolyl 4-hydroxylase β-subunit (P4Hβ) operably linked to a promoter functional in said yeast host cell, and (iii) a third DNA molecule comprising a DNA sequence encoding a polypeptide or peptide operably linked to a promoter functional in said yeast host cell, wherein said polypeptide or peptide is one which, when hydroxylated, forms said hydroxylated triple helical protein, and wherein said polypeptide or peptide is a synthetic polypeptide or peptide represented by the following formula:

$(A)_l$—$(B)_m$—$(GlyXY)_n$—$(C)_o$—$(D)_p$, wherein GlyXY represents a triple helical forming repeating sequence, wherein Gly represents glycine, wherein X and Y, which may be the same or different, each represent an amino acid, and wherein the identity of each amino acid represented by X and Y may vary from GlyXY triplet to GlyXY triplet, but wherein at least one Y in the triple helical forming repeating sequence $(GlyXY)_n$ is proline, wherein A and D each represent a polypeptide or peptide domain which optionally comprises a triple helical forming repeating sequence $(GlyXY)_n$, wherein B and C each represent a polypeptide or peptide domain which is heterologous to collagen proteins and which does not comprise a triple helical forming repeating sequence $(GlyXY)_n$, wherein n is an integer of from 2 to 1500, wherein each of m and o is 1 and each of l and p are selected from 0 and 1, and (B) culturing the resulting yeast host cell of step (A) under conditions suitable to express said P4Hα, said P4Hβ and said polypeptide or peptide, to produce said hydroxylated triple helical protein, and wherein during culturing in step (B), each of said first DNA molecule, said second DNA molecule and said third DNA molecule are replicated, stably retained and segregated by the yeast host cell.

32. The method of claim 31, wherein expression of said P4Hα and said P4Hβ is controlled in a coordinated manner by a bidirectional promoter.

33. The method according to claim 31, wherein said P4Hα is an avian P4Hα or a mammalian P4Hα, and said P4Hβ is an avian P4Hβ or a mammalian P4Hβ.

34. The method according to claim 31, wherein each of said first DNA molecule, said second DNA molecule and said third DNA molecule further comprise a DNA sequence encoding a secretion signal such that P4H and said polypeptide or peptide are expressed and secreted by said yeast host cell.

35. The method according to claim 31, wherein in step (A) each of said first DNA molecule, said second DNA molecule and said third DNA molecule is present on the same vector, or on different vectors, and wherein said vector or vectors comprise a centromere (CEN) sequence.

36. The method according to claim 31, wherein in step (A), at least one of said first DNA molecule, said second DNA molecule and said third DNA molecule is present on the same vector and said vector comprises a CEN sequence, and at least one of said first DNA molecule, said second DNA molecule and said third DNA molecule is present on a high copy number vector, which may be the same vector or different vectors.

37. The method according to claim 31, wherein said yeast host cell is a member of a genus selected from the group consisting of Kluveromyces, Saccharomyces, Schizosaccharomyces, Yarrowia and Pichia.

38. The method according to claim 31, wherein the triple helical forming repeating sequence $(GlyXY)_n$ includes at least one integrin binding site.

39. The method according to claim 32, wherein said bidirectional promoter is yeast GAL1-10 bidirectional promoter.

40. The method according to claim 33, wherein said mammalian P4Hα is human P4Hα, and said mammalian P4Hβ is human P4Hβ.

41. The method according to claim 35, wherein said vector which comprises a CEN sequence is a YAC vector.

42. The method according to claim 36, wherein said vector which comprises a CEN sequence is a YAC vector.

43. The method according to claim 36, wherein said high copy number vector is a Yep plasmid.

44. The method according to claim 38, wherein the integrin binding site comprises the amino acid sequence: GLAGAPGLR (SEQ ID NO:38).

45. The method according to claim 41, wherein said first DNA molecule, said second DNA molecule and said third DNA molecule are present on the same YAC vector.

46. A yeast host cell which produces a hydroxylated triple helical protein upon culturing, wherein said yeast host cell comprises;
(A) a first DNA molecule comprising a DNA sequence encoding prolyl 4-hydroxylase α-subunit (P4Hα) operably linked to a promoter functional in said yeast host cell,
(B) a second DNA molecule comprising a DNA sequence encoding prolyl 4-hydroxylase β-subunit (P4Hβ) operably linked to a promoter functional in said yeast host cell, and
(C) a third DNA molecule comprising a DNA sequence encoding a polypeptide or peptide operably linked to a promoter functional in said yeast host cell, wherein said polypeptide or peptide is one which, when hydroxylated, forms said hydroxylated triple helical protein, and wherein said polypeptide or peptide is a synthetic polypeptide or peptide represented by the following formula:

$$(A)_l-(B)_m-(GlyXY)_n-(C)_o-(D)_p,$$

wherein GlyXY represents a triple helical forming repeating sequence,
wherein Gly represents glycine,
wherein X and Y, which may be the same or different, each represent an amino acid, and wherein the identity of each amino acid represented by X and Y may vary from GlyXY triplet to GlyXY triplet, but wherein at least one Y in the triple helical forming repeating sequence $(GlyXY)_n$ is proline,
wherein A and D each represent a polypeptide or peptide domain which optionally comprises a triple helical forming repeating sequence $(GlyXY)_n$,
wherein B and C each represent a polypeptide or peptide domain which is heterologous to collagen proteins and which does not comprise a triple helical forming repeating sequence $(GlyXY)_n$,
wherein n is an integer of from 2 to 1500,
wherein each of m and o is 1 and each of l and p are selected from 0 and 1, and
wherein upon culturing of said yeast host cell, each of said first DNA molecule, said second DNA molecule and said third DNA molecule are replicated, stably retained and segregated by said yeast host cell.

47. The yeast host cell of claim 46, wherein expression of said P4Hα and said P4Hβ is controlled in a coordinated manner by a bidirectional promoter.

48. The yeast host cell according to claim 46, wherein said P4Hα is an avian P4Hα or a mammalian P4Hα, and said P4Hβ is an avian P4Hβ or a mammalian P4Hβ.

49. The yeast host cell according to claim 46, wherein each of said first DNA molecule, said second DNA molecule and said third DNA molecule further comprise a DNA sequence encoding a secretion signal such that P4H and said polypeptide or peptide are expressed and secreted by said yeast host cell.

50. The yeast host cell according to claim 46, wherein in step (A) each of said first DNA molecule, said second DNA molecule and said third DNA molecule is present on the same vector, or on different vectors, wherein said vector or vectors comprise a centromere (CEN) sequence.

51. The yeast host cell according to claim 46, wherein in step (A), at least one of said first DNA molecule, said second DNA molecule and said third DNA molecule is present on the same vector and said vector comprises a CEN sequence, and at least one of said first DNA molecule, said second DNA molecule and said third DNA molecule is present on a high copy number vector, which may be the same vector or different vectors.

52. The yeast host cell according to claim 46, wherein said yeast host cell is a member of a genus selected from the group consisting of Kluveromyces, Saccharomyces, Schizosaccharomyces, Yarrowia and Pichia.

53. The yeast host cell according to claim 46, wherein the triple helical forming repeating sequence $(GlyXY)_n$ includes at least one integrin binding site.

54. The yeast host cell according to claim 47, wherein said bidirectional promoter is yeast GAL1-10 bidirectional promoter.

55. The yeast host cell according to claim 48, wherein said mammalian P4Hα is human P4Hα, and said mammalian P4Hβ is human P4Hβ.

56. The yeast host cell according to claim 50, wherein said vector which comprises a CEN sequence is a YAC vector.

57. The yeast host cell according to claim 51, wherein said vector which comprises a CEN sequence is a YAC vector.

58. The yeast host cell according to claim 51, wherein said high copy number vector is a Yep plasmid.

59. The yeast host cell according to claim 53, wherein the integrin binding site comprises the amino acid sequence: GLAGAPGLR (SEQ ID NO:38).

60. The yeast host cell according to claim 56, wherein said first DNA molecule, said second DNA molecule and said third DNA molecule are present on the same YAC vector.

* * * * *

```
                              SEQUENCE LISTING

<160> NUMBER OF SEQ ID NOS: 43

<210> SEQ ID NO 1
<211> LENGTH: 26
<212> TYPE: DNA
<213> ORGANISM: synthetic construct

<400> SEQUENCE: 1
ctgtagagga tccccgggta cggagc                                          26

<210> SEQ ID NO 2
<211> LENGTH: 23
<212> TYPE: DNA
<213> ORGANISM: synthetic construct

<400> SEQUENCE: 2
ttatattgaa ttctcaaaaa ttc                                             23

<210> SEQ ID NO 3
<211> LENGTH: 32
<212> TYPE: DNA
<213> ORGANISM: synthetic construct

<400> SEQUENCE: 3
tgtaaaatta aaggatccca aagatgtggt at                                   32

<210> SEQ ID NO 4
<211> LENGTH: 30
<212> TYPE: DNA
<213> ORGANISM: synthetic construct

<400> SEQUENCE: 4
gccgggatcc tgtcattcca atgacaacgt                                      30

<210> SEQ ID NO 5
<211> LENGTH: 44
<212> TYPE: DNA
<213> ORGANISM: synthetic construct

<400> SEQUENCE: 5
actggacgga tcccgagcgc cccgcctgct ccgtgtccga catg                      44

<210> SEQ ID NO 6
<211> LENGTH: 24
<212> TYPE: DNA
<213> ORGANISM: synthetic construct

<400> SEQUENCE: 6
ggttctcctt ggtgacctcc cctt                                            24

<210> SEQ ID NO 7
<211> LENGTH: 24
<212> TYPE: DNA
<213> ORGANISM: synthetic construct
```

<400> SEQUENCE: 7 gaagggagg tcaccaagga gaac                                             24

<210> SEQ ID NO 8
<211> LENGTH: 36
<212> TYPE: DNA
<213> ORGANISM: synthetic construct

<400> SEQUENCE: 8
ccttcaggat cctattagac ttcatctttc aacagc                               36

<210> SEQ ID NO 9
<211> LENGTH: 44
<212> TYPE: DNA
<213> ORGANISM: synthetic construct

<400> SEQUENCE: 9
actggacgga tcccgagcgc cccgcctgct ccgtctccga catg                      44

<210> SEQ ID NO 10
<211> LENGTH: 35
<212> TYPE: DNA
<213> ORGANISM: synthetic construct

<400> SEQUENCE: 10
ccttcaggat cctattagac ttcatctttc acagc                                35

<210> SEQ ID NO 11
<211> LENGTH: 39
<212> TYPE: DNA
<213> ORGANISM: synthetic construct

<400> SEQUENCE: 11
ctagttgaat tctacacaat gctgcgccgc gctctgctg                            39

<210> SEQ ID NO 12
<211> LENGTH: 36
<212> TYPE: DNA
<213> ORGANISM: synthetic construct

<400> SEQUENCE: 12
gcaatggaat tcttattaca gttcgtgcac agcttt                               36

<210> SEQ ID NO 13
<211> LENGTH: 4
<212> TYPE: PRT
<213> ORGANISM: Yeast Endoplasmic Reticulum Retention Signal

<400> SEQUENCE: 13

His Asp Glu Leu
 1

<210> SEQ ID NO 14
<211> LENGTH: 5
<212> TYPE: PRT
<213> ORGANISM: Mammalian Endoplasmic Reticulum Retention Signal

<400> SEQUENCE: 14

Lys Asp Ala Glu Leu
 1               5

<210> SEQ ID NO 15
<211> LENGTH: 42

-continued

```
<212> TYPE: DNA
<213> ORGANISM: synthetic construct

<400> SEQUENCE: 15
gctagcaagc ttggagctcc aggcccactt gggattgctg gg                          42

<210> SEQ ID NO 16
<211> LENGTH: 45
<212> TYPE: DNA
<213> ORGANISM: synthetic construct

<400> SEQUENCE: 16
tcgcgatcta gattataaaa agcaaacagg gccaacgtcc acacc                       45

<210> SEQ ID NO 17
<211> LENGTH: 6
<212> TYPE: DNA
<213> ORGANISM: synthetic construct

<400> SEQUENCE: 17 gctagc                                                                   6

<210> SEQ ID NO 18
<211> LENGTH: 6
<212> TYPE: DNA
<213> ORGANISM: synthetic construct

<400> SEQUENCE: 18 aagctt                                                                   6

<210> SEQ ID NO 19
<211> LENGTH: 6
<212> TYPE: DNA
<213> ORGANISM: synthetic construct

<400> SEQUENCE: 19 tctaga                                                                   6

<210> SEQ ID NO 20
<211> LENGTH: 6
<212> TYPE: DNA
<213> ORGANISM: synthetic construct

<400> SEQUENCE: 20 tcgcga                                                                   6

<210> SEQ ID NO 21
<211> LENGTH: 21
<212> TYPE: PRT
<213> ORGANISM: synthetic construct

<400> SEQUENCE: 21

Asp Tyr Lys Asp Asp Asp Asp Lys Ala Ser Lys Leu Gly Ala Pro Gly
 1               5                  10                  15

Pro Leu Gly Ile Ala
            20

<210> SEQ ID NO 22
<211> LENGTH: 9
<212> TYPE: PRT
<213> ORGANISM: synthetic construct

<400> SEQUENCE: 22
```

Gly Pro Pro Gly Pro Pro Gly Leu Ala
1               5

<210> SEQ ID NO 23
<211> LENGTH: 9
<212> TYPE: PRT
<213> ORGANISM: synthetic construct

<400> SEQUENCE: 23

Gly Pro Pro Gly Pro Pro Gly Glu Arg
1               5

<210> SEQ ID NO 24
<211> LENGTH: 9
<212> TYPE: PRT
<213> ORGANISM: synthetic construct

<400> SEQUENCE: 24

Gly Pro Pro Gly Pro Pro Gly Pro Ala
1               5

<210> SEQ ID NO 25
<211> LENGTH: 9
<212> TYPE: PRT
<213> ORGANISM: synthetic construct

<400> SEQUENCE: 25

Gly Pro Pro Gly Pro Pro Gly Ala Pro
1               5

<210> SEQ ID NO 26
<211> LENGTH: 9
<212> TYPE: PRT
<213> ORGANISM: synthetic construct

<400> SEQUENCE: 26

Gly Leu Ala Gly Ala Pro Gly Leu Arg
1               5

<210> SEQ ID NO 27
<211> LENGTH: 45
<212> TYPE: PRT
<213> ORGANISM: synthetic construct

<400> SEQUENCE: 27

Gly Gly Lys Gly Asp Ala Gly Ala Pro Gly Glu Arg Gly Pro Pro Gly
1               5                   10                  15

Leu Ala Gly Ala Pro Gly Leu Arg Gly Gly Ala Gly Pro Pro Gly Pro
            20                  25                  30

Glu Gly Gly Lys Gly Ala Ala Gly Pro Pro Gly Pro Pro
        35                  40                  45

<210> SEQ ID NO 28
<211> LENGTH: 7
<212> TYPE: PRT
<213> ORGANISM: synthetic construct

<400> SEQUENCE: 28

Met Gly Ala Pro Gly Ala Pro
1               5

<210> SEQ ID NO 29
<211> LENGTH: 6
<212> TYPE: PRT

<213> ORGANISM: synthetic construct

<400> SEQUENCE: 29

Gly Ala Pro Gly Ala Pro
 1               5

<210> SEQ ID NO 30
<211> LENGTH: 7
<212> TYPE: PRT
<213> ORGANISM: synthetic construct

<400> SEQUENCE: 30

Gly Leu Glu Gly Pro Arg Gly
 1               5

<210> SEQ ID NO 31
<211> LENGTH: 26
<212> TYPE: DNA
<213> ORGANISM: synthetic construct

<400> SEQUENCE: 31
aattccatgg gtgctccagg tgctcc                                    26

<210> SEQ ID NO 32
<211> LENGTH: 22
<212> TYPE: DNA
<213> ORGANISM: synthetic construct

<400> SEQUENCE: 32
ggccacctgg tggacctggt gg                                        22

<210> SEQ ID NO 33
<211> LENGTH: 22
<212> TYPE: DNA
<213> ORGANISM: synthetic construct

<400> SEQUENCE: 33
ggcccggtgg taagggtgac gc                                        22

<210> SEQ ID NO 34
<211> LENGTH: 20
<212> TYPE: DNA
<213> ORGANISM: synthetic construct

<400> SEQUENCE: 34
cgcgcacctg gtggacctgg                                           20

<210> SEQ ID NO 35
<211> LENGTH: 25
<212> TYPE: DNA
<213> ORGANISM: synthetic construct

<400> SEQUENCE: 35
cgcgcggtgg taagggtgac gctgg                                     25

<210> SEQ ID NO 36
<211> LENGTH: 41
<212> TYPE: DNA
<213> ORGANISM: synthetic construct

<400> SEQUENCE: 36
acaaccctgg tggacctggt ggacctggtg gacctgggtg g                   41

<210> SEQ ID NO 37
<211> LENGTH: 40
<212> TYPE: DNA
<213> ORGANISM: synthetic construct

<400> SEQUENCE: 37
ctagccccgc ggaccctcga gaccacaaca accctggtgg                40

<210> SEQ ID NO 38
<211> LENGTH: 9
<212> TYPE: PRT
<213> ORGANISM: synthetic construct

<400> SEQUENCE: 38

Gly Leu Ala Gly Ala Pro Gly Leu Arg
  1               5

<210> SEQ ID NO 39
<211> LENGTH: 1572
<212> TYPE: DNA
<213> ORGANISM: Collagen Type III Alpha I Chain

<400> SEQUENCE: 39
ccaggcccac ttgggattgc tgggatcact ggagcacggg gtcttgcagg accaccaggc      60
atgccaggtc ctaggggaag ccctggccct caggtgtca aggtgaaag tgggaaacca      120
ggagctaacg gtctcagtgg agaacgtggt ccccctggac cccagggtct tcctggtctg      180
gctggtacag ctggtgaacc tggaagagat ggaaaccctg atcagatgg tcttccaggt      240
cgagatggat ctcctggtgg caagggtgat cgtggtgaaa atggctctcc tggtgcccct      300
ggcgctcctg gtcatccagg cccacctggt cctgtcggtc cagctggaaa gagtggtgac      360
agaggagaaa gtggccctgc tggccctgct ggtgctcccg gtcctgctgg ttcccgaggt      420
gctcctggtc tcaaggccc acgtggtgac aaaggtgaaa caggtgaacg tggagctgct      480
ggcatcaaag gacatcgagg attccctggt aatccaggtg ccccaggttc tccaggccct      540
gctggtcagc agggtgcaat cggcagtcca ggacctgcag gccccagagg acctgttgga      600
cccagtggac ctcctggcaa agatggaacc agtggacatc caggtcccat ggaccacca      660
gggcctcgag gtaacagagg tgaaagagga tctgagggct ccccaggcca cccagggcaa      720
ccaggcccctc ctggacctcc tggtgcccct ggtccttgct gcggtggtgt tggagccgct      780
gccattgctg ggattggagg tgaaaaagct ggcggttttg cccgtatta tggacctgaa      840
ccaatggatt tcaaaatcaa caccgatgag attatcactt cactcaagtc tgttaatgga      900
caaatagaaa gcctcattag tcctgatggt tctcgtaaaa accccgctag aaactgcaga      960
gacctgaaat tctgccatcc tgaactcaag actggagaat actgggtcga ccctaaccaa     1020
ggatgcaaat tggatgctat caaggtattc tgtaatatgg aaactgggga acatgcata     1080
agtgccaatc ctttgaatgt tccacggaaa cactggtgga cagattctag tgctgagaag     1140
aaacacgttt ggtttggaga gtccatcgat ggtggttttc agtttagcta cggcaatcct     1200
gaacttcctg aagatgtcct tgatgtgcag ctggcattcc ctcgacttct ctccagccga     1260
gcttcccaga acatcacata tcactgcaaa aatagcattg catacatgga tcaggccagt     1320
ggaaatgtaa agaaggccct gaagctgatg gggtcaaatg aaggtgaatt caaggctgaa     1380
ggaaatagca aattcaccta cacagttctg gaggatggtt gcacgaaaca cactgggaa      1440
tggagcaaaa cagtctttga atatcgaaca cgcaaggctg tgagactacc tattgtagat     1500
attgcacccct atgacattgg tggtcctgat caagaatttg gtgtggacgt tggccctgtt     1560 tgcttttttat aa 1572

<210> SEQ ID NO 40
<211> LENGTH: 503
<212> TYPE: DNA
<213> ORGANISM: synthetic construct

<400> SEQUENCE: 40

```
gaattccatg ggtgctccag gtgctccagg tggtaagggt gacgctggtg ctccaggtga    60
aagaggtcca ccaggtttgg ctggtgctcc aggtttgaga ggtggtgctg gtccaccagg   120
tccagaaggt ggtaagggtg ctgctggtcc accaggtcca ccaggtgggc ccggtggtaa   180
gggtgacgct ggtgctccag gtgaaagagg tccaccaggt ttggctggtg ctccaggttt   240
gagaggtggt gctggtccac aggtccagaa ggtggtaagg gtgctgctgg tccaccaggt   300
ccaccaggt gcgcgcggtg gtaagggtga cgctggtgct ccaggtgaaa gaggtccacc   360
aggtttggct ggtgctccag gtttgagagg tggtgctggt ccaccaggtc agaaggtgg   420
taagggtgct gctggtccac aggtccacc aggtccacca ggtccaccag gttgttgtgg   480
tctcgagggt ccgcggggct agc                                          503
```

<210> SEQ ID NO 41
<211> LENGTH: 166
<212> TYPE: PRT
<213> ORGANISM: synthetic construct

<400> SEQUENCE: 41

Asn Ser Met Gly Ala Pro Gly Ala Pro Gly Gly Lys Gly Asp Ala Gly
1               5                   10                  15

Ala Pro Gly Glu Arg Gly Pro Pro Gly Leu Ala Gly Ala Pro Gly Leu
                20                  25                  30

Arg Gly Gly Ala Gly Pro Pro Gly Pro Glu Gly Gly Lys Gly Ala Ala
            35                  40                  45

Gly Pro Pro Gly Pro Pro Gly Gly Pro Gly Gly Lys Gly Asp Ala Gly
        50                  55                  60

Ala Pro Gly Glu Arg Gly Pro Pro Gly Leu Ala Gly Ala Pro Gly Leu
65                  70                  75                  80

Arg Gly Gly Ala Gly Pro Pro Gly Pro Glu Gly Gly Lys Gly Ala Ala
                85                  90                  95

Gly Pro Pro Gly Pro Pro Gly Ala Arg Gly Gly Lys Gly Asp Ala Gly
            100                 105                 110

Ala Pro Gly Glu Arg Gly Pro Pro Gly Leu Ala Gly Ala Pro Gly Leu
        115                 120                 125

Arg Gly Gly Ala Gly Pro Pro Gly Pro Glu Gly Gly Lys Gly Ala Ala
    130                 135                 140

Gly Pro Pro Gly Pro Pro Gly Pro Pro Gly Pro Pro Gly Cys Cys Gly
145                 150                 155                 160

Leu Glu Gly Pro Arg Gly
                165

<210> SEQ ID NO 42
<211> LENGTH: 4
<212> TYPE: PRT
<213> ORGANISM: Endoplasmic Reticulum Retention Signal

<400> SEQUENCE: 42

Lys Asp Glu Leu

```
<210> SEQ ID NO 43
<211> LENGTH: 4
<212> TYPE: PRT
<213> ORGANISM: Endoplasmic Reticulum Retention Signal

<400> SEQUENCE: 43

Lys Glu Glu Leu
```